United States Patent
Gizaw et al.

(10) Patent No.: US 8,075,637 B2
(45) Date of Patent: Dec. 13, 2011

(54) MODIFIED LIGNIN BIOPOLYMER USEFUL IN CLEANING COMPOSITIONS

(75) Inventors: Yonas Gizaw, West Chester, OH (US);
Bruno Albert Jean Hubesch, Neerijse-Huldenberg (BE); Jeffrey Scott Dupont, Cincinnati, OH (US); Xiaoru Jenny Wang, Mason, OH (US); Luke Andrew Zannoni, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/562,209

(22) Filed: Sep. 18, 2009

(65) Prior Publication Data

US 2010/0075878 A1    Mar. 25, 2010

Related U.S. Application Data

(60) Provisional application No. 61/098,286, filed on Sep. 19, 2008.

(51) Int. Cl.
C11D 3/382 (2006.01)
C11D 3/37 (2006.01)
C08H 6/00 (2010.01)
B08B 3/04 (2006.01)

(52) U.S. Cl. ............ 8/137; 510/462; 510/464; 510/492; 510/499

(58) Field of Classification Search ............ 510/462, 510/464, 492, 499; 8/137
See application file for complete search history.

(56) References Cited

U.S. PATENT DOCUMENTS

| 3,061,551 | A |   | 10/1962 | Rutenberg et al. |
| 3,580,853 | A |   | 5/1971  | Parran |
| 3,865,803 | A |   | 2/1975  | Falkehag |
| 4,775,744 | A |   | 10/1988 | Schilling et al. |
| 4,797,157 | A |   | 1/1989  | Dilling et al. |
| 5,972,047 | A | * | 10/1999 | Dilling et al. ............ 8/552 |
| 2010/0075879 | A1 |   | 3/2010 | Gizaw et al. |
| 2010/0075880 | A1 |   | 3/2010 | Dupont et al. |
| 2010/0075887 | A1 |   | 3/2010 | Wang et al. |

FOREIGN PATENT DOCUMENTS

| DE | 10 2004 063766 A1 |   | 7/2006 |
| EP | 0 752 468 B1 |   | 8/2003 |
| EP | 1927616 A2 |   | 6/2008 |
| EP | 1 194 461 B1 |   | 10/2008 |
| GB | 699 530 A |   | 11/1953 |
| WO | WO 98/29528 A2 |   | 7/1998 |
| WO | WO 99/14245 A1 |   | 3/1999 |
| WO | WO 03/062254 | * | 7/2003 |
| WO | WO 03/062254 A1 |   | 7/2003 |
| WO | WO 2008/034674 A1 |   | 3/2008 |
| WO | WO 2008/046174 A1 |   | 4/2008 |
| WO | WO 2009/010911 A2 |   | 1/2009 |

OTHER PUBLICATIONS

PCT International Search Report, date mailed Feb. 15, 2010, 10 pages.

* cited by examiner

*Primary Examiner* — Brian P Mruk
(74) *Attorney, Agent, or Firm* — Stephen T. Murphy; Steven W. Miller; Leonard W. Lewis

(57) ABSTRACT

Novel modified lignin polymers containing anionic, cationic, and/or alkoxy substitution are disclosed. Further, new cleaning compositions including the novel substituted lignin polymers are disclosed. Methods of forming the modified lignin polymers and cleaning compositions are disclosed.

18 Claims, 2 Drawing Sheets

MODIFIED LIGNIN BIOPOLYMER USEFUL IN CLEANING COMPOSITIONS

This application claims benefit of 61/098,286, filed on Sep. 19, 2008.

FIELD OF THE INVENTION

The present invention is related to modified lignin biopolymers that are useful as an ingredient to a variety of consumer products. Modified lignin biopolymers having a unique structure are presented. In addition, the biopolymers of the present invention may provide benefits in fabric care products and other cleaning products or applications where cleaning of a surface is needed.

BACKGROUND OF THE INVENTION

Lignin is a component of all vascular plants, found mostly between cellular structures but also within the cells and in the cell walls. It functions to regulate the transport of liquid in the plant (in part by reinforcing cell walls and keeping them from collapsing and in part by regulating the flow of liquid) and enables the plant to grow tall and compete for sunshine. Lignin is a complex, amorphous, three-dimensional polymer having a structure based on phenylpropane. In the natural unprocessed form, the molecular structure of lignin varies according to the source and is so complex and varied that its molecular structure has never been completely described.

There are three common monomers that make up almost all lignin found in nature. These common monomers are p-coumaryl alcohol, coniferyl alcohol, and sinapyl alcohol as shown in Scheme 1. These monomers are biosynthesized in plants via the shikimic acid pathway. p-Coumaryl alcohol is a component of grass and forage-type lignin. Coniferyl alcohol is the predominant lignin monomer found in softwoods and both coniferyl and sinapyl alcohols are the major building blocks of hardwood lignin.

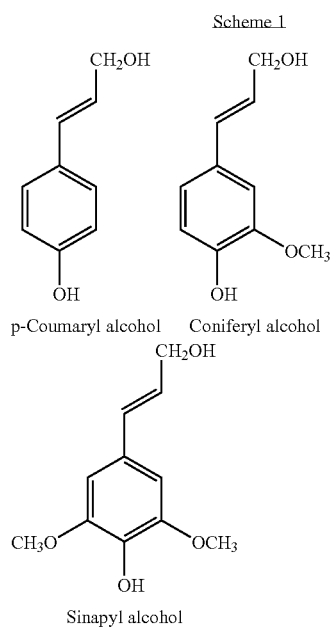

Scheme 1

Improved cleaning is a constant aim for detergent manufacturers. In spite of the use of many effective surfactants, synthetic polymers, and combinations thereof, many surfactant-based products still do not achieve complete cleaning of soiled objects, especially when used at low water temperatures.

Fabric, especially clothing, can become soiled with a variety of foreign substances ranging from hydrophobic stains (grease, oil) to hydrophilic stains (clay). The level of cleaning which is necessary to remove these foreign substances depends to a large degree upon the amount of stain present and the degree to which the foreign substance has contacted the fabric fibers. For example, grass stains usually involve direct abrasive contact with vegetative matter thereby producing highly penetrating stains. Many cleaning formulations use combinations of enzymes to aid in the peptization and removal of these stains. Alternatively, clay soil stains provide a different type of soil removal problem due to the high degree of charge associated with the clay itself. This high surface charge density resists any appreciable peptization and dispersal of the clay by conventional surfactants and enzymes. For these soils, peptizing polymers and builders aid in the removal of the soils. Finally, hydrophobic stains, such as greases and oils, usually involve another soil removal problem since technologies that remove grass stains and outdoor soil stains (clay) do not effectively aid in grease removal. For these hydrophobic stains, a surfactant or combination of surfactants is generally preferred for removal.

In addition to soil removal, for effective cleaning it is also important that the soil or staining material, once removed from the surface does not re-deposit onto the surface during the wash treatment process. That is, once the soil or staining material is removed from the surface, the cleaning product must prevent the soil or staining material from redepositing onto the clean surface and instead be removed from the wash process.

Sudsing profile of a detergent or cleaning composition, including but not be limited to speed and volume of suds generated upon dissolving the detergent composition in a washing solution, retention of suds during washing cycle and ease in rinsing the suds in the rinsing cycle is highly valued by consumers. Suds are viewed by such consumers as an important signal that detergent is "working" and is an active driver of accomplishing their cleaning objectives. Thus, rapidly generated high volume of suds and well retained suds during washing cycle are highly preferred. On the other hand, high volume of suds in the washing cycle typically results in suds being carried over to the rinse bath solution and requiring additional time, energy and water to thoroughly rinse the laundered or cleaned items. Accordingly, quick collapse of suds in rinsing solution is another preferred aspect of the sudsing profile of a detergent composition.

In laundry applications, current soil release polymers ("SRP") are generally effective on polyester or other synthetic fabrics where the grease, oil or similar hydrophobic stains spread out and form an attached film and thereby are not easily removed in an aqueous laundering process. Many soil release polymers have a less dramatic effect on "blended" fabrics, that is on fabrics that comprise a mixture of cotton and synthetic material, and have little or no effect on cotton articles. There is a long felt need in the art for laundry detergent compositions that contain soil release polymers, including polymers from natural renewable resources, that can effectively modify the fabric surface, such as cotton fabrics, to aid in the removal of many types of both hydrophilic and hydrophobic soils from fabric.

For these reasons and others, an effective cleaning composition is typically comprised of many technologies that aid in removal of a variety of soils. Unfortunately, due to cost and formulation constraints, it is rare to find a cleaning formulation that effectively incorporates each of the above cleaning technologies to completely remove all of the target soils and stains during a cleaning process.

Other detergent products, such as, for example, hard surface cleaners, such as dish washing detergents, and those used in the health, beauty, and personal care area, including shampoos and soaps, may also benefit from products having improved cleaning/Sudsing/soil release properties.

There is a long felt need in the art for cleaning compositions that contain improved materials, such as polymers, that demonstrate these effects on hydrophilic and hydrophobic soils and staining materials on fabrics, hard surfaces and other soiled surfaces. In addition, as the effectiveness of the active polymer increases there is less of a burden on the other cleaning technologies so that one could formulate using less of these materials, use more cost effective materials and/or leverage improved cleaning to drive consumer noticeability.

SUMMARY OF THE INVENTION

The present disclosure relates to novel modified lignin polymers which may be incorporated into a cleaning composition. According to one embodiment, the present disclosure provides a modified lignin polymer comprising a randomly substituted lignin backbone comprising substituted lignin monomer residues and unsubstituted lignin monomer residues. At least two or more of the hydroxyl groups on the randomly substituted lignin backbone have been substituted with R substituent groups. Each R substituent group is independently an R substituent type selected from the group consisting of nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types. For example, the lignin backbone may comprise $R^1$ and $R^2$ substituent types; $R^1$ and $R^3$ substituent types; $R^2$ and $R^3$ substituent types; or $R^1$, $R^2$ and $R^3$ substituent types.

According to another embodiment, the present disclosure provides a modified lignin polymer comprising a randomly substituted lignin backbone having a structure represented by Formula I:

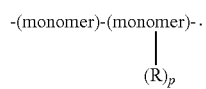

The randomly substituted lignin backbone comprises substituted lignin monomer residues and unsubstituted lignin monomer residues selected from the group consisting of substituted and unsubstituted residues of p-coumaryl alcohol, substituted and unsubstituted residues of coniferyl alcohol, substituted and unsubstituted residues of sinapyl alcohol, derivatives thereof, and mixtures thereof. At least two or more of the hydroxyl groups on the randomly substituted lignin backbone have been substituted with R substituent groups and "p" is an integer from 1 to 3. Each R substituent group is independently an R substituent type selected from the group consisting of: nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types. Each $R^1$ group independently has a structure according to Formula II:

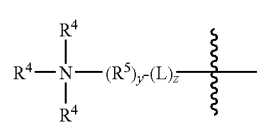

where each $R^4$ is independently selected from the group consisting of a lone pair of electrons, H, $CH_3$, and linear or branched, saturated or unsaturated $C_2$-$C_{18}$ alkyl, provided that at least two of the $R^4$ groups are not a lone pair of electrons; $R^5$ is a linear or branched, saturated or unsaturated $C_2$-$C_{18}$ alkyl chain or a linear or branched, saturated or unsaturated secondary hydroxy($C_2$-$C_{18}$)alkyl chain; L is a linking group selected from the group consisting of —O—, —C(O)O—, —$NR^6$—, —C(O)$NR^6$—, and —$NR^6$C(O)$NR^6$—, where $R^6$ is H or $C_1$-$C_6$ alkyl; y has a value of 0 or 1; and z has a value of 0 or 1. Each $R^2$ group independently has a structure according to Formula III:

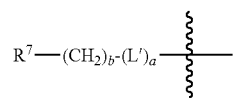

wherein $R^7$ is an anionic group selected from the group consisting of carboxylate, carboxymethyl, succinate, sulfate, sulfonate, arylsulfonate, phosphate, phosphonate, dicarboxylate, and polycarboxylate; L' is a linking group selected from the group consisting of —O—, —C(O)O—, —$NR^8$—, —C(O)$NR^8$—, and —$NR^8$C(O)$NR^8$—, where $R^8$ is H or $C_1$-$C_6$ alkyl; a has a value of 0 or 1; and b is an integer from 0 to 18. Each $R^3$ group independently has a structure according to Formula IV:

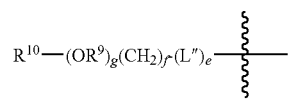

wherein e has a value of 0 or 1; f is an integer from 0 to 8; g is an integer from 0 to 50; L" is a linking group selected from the group consisting of —O—, —C(O)O—, —$NR^{11}$—, —C(O)$NR^{11}$—, and —$NR^{11}$C(O)$NR^{11}$—, where $R^{11}$ is H or $C_1$-$C_6$ alkyl; each $R^9$ is the group ethylene, propylene, butylene, or mixtures thereof; and $R^{10}$ is an end group selected from the group consisting of hydrogen, $C_1$-$C_{20}$ alkyl, hydroxy, —$OR^1$ and —$OR^2$.

Further embodiments of the present disclosure provide for a cleaning composition comprising a modified lignin polymer having a randomly substituted lignin backbone. The randomly substituted lignin backbone comprises substituted lignin monomer residues and unsubstituted lignin monomer residues, where at least two or more of the hydroxyl groups on the randomly substituted lignin backbone have been substituted with R substituent groups. Each R substituent group is independently an R substituent type selected from the group consisting of nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types.

Still further embodiments of the present disclosure provide for methods of making a cleaning composition comprising adding a modified lignin polymer to the cleaning composition. According to these embodiments, the modified lignin polymer composition may be any of the modified lignin polymer compositions described and disclosed herein, such as the modified lignin polymers having a randomly substituted lignin backbone, as set forth herein. Methods of treating a substrate comprising contacting the substrate with an effective amount of a cleaning composition comprising the modified lignin polymers described herein are also disclosed. Examples of substrates include, but are not limited to, fabrics and textiles, hard and soft surfaces, dishes, hair, and skin.

BRIEF DESCRIPTION OF THE DRAWINGS

The various embodiments of the present disclosure may be better understood when considered along with the following figures.

DETAILED DESCRIPTION OF THE INVENTION

Definitions

Figure 1:
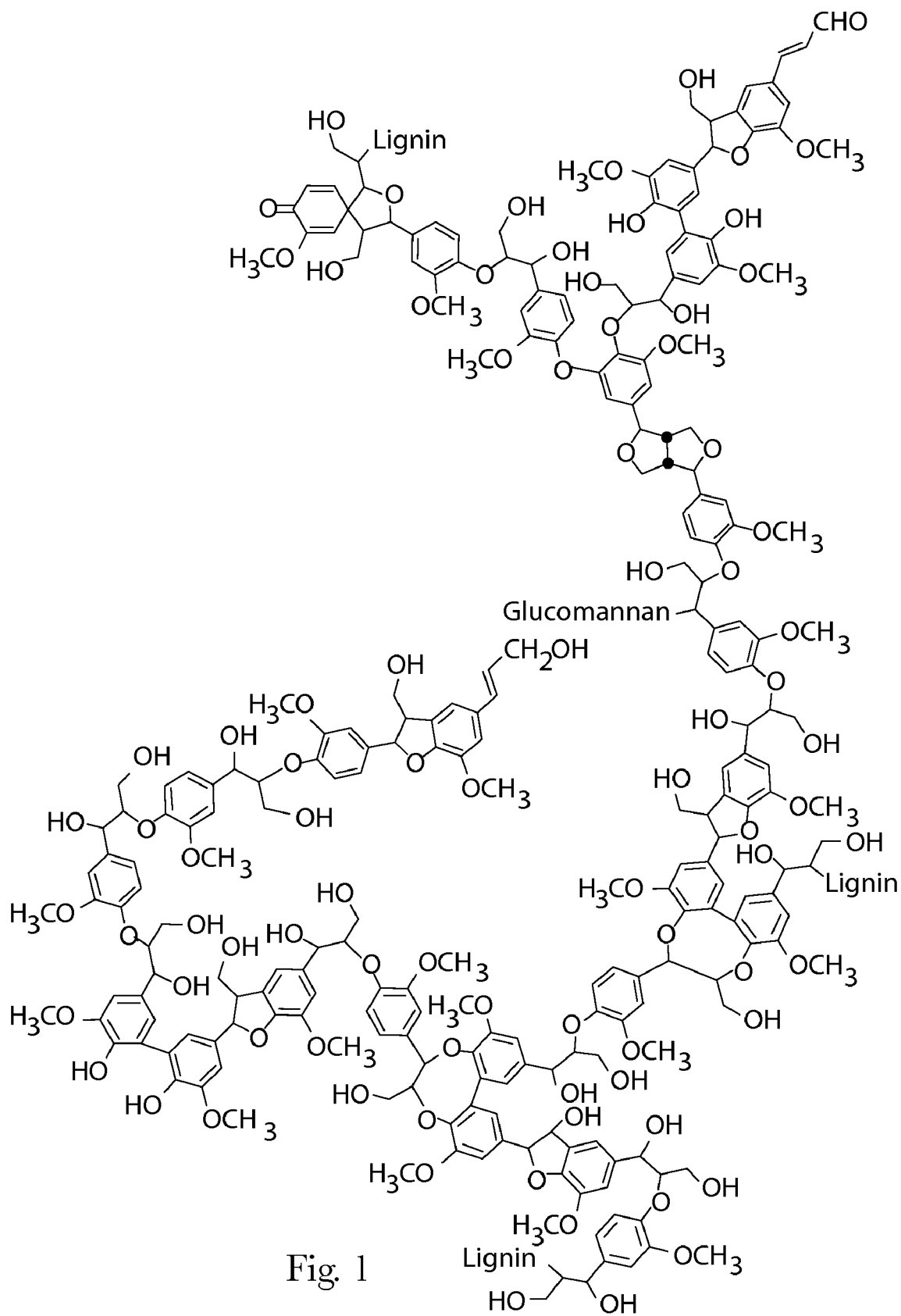
FIGS. 1 and 2 illustrate exemplary structures of an unmodified lignin polymer.

As used herein, the term "lignin" includes oligomeric and polymeric structures derived from wood and other plant sources and is an integral part of the cell walls of plants. Lignin is typically removed prior to the production of paper products or is a byproduct of other industries which involve the manipulation of plant material. The lignin molecular structure is complex and random, comprising primarily substituted phenylpropane monomers polymerized in a seemingly random and unorganized fashion. See, for example, FIGS. 1 and 2. Lignin structure may vary depending, for example, at least in part, on the plant source and isolation process.

As used herein, the term "lignin backbone" includes the carbon skeleton of the lignin polymer which may be derived from the carbons in the lignin monomer units. The lignin backbone further includes the ether linkages between the carbons of adjacent monomer units, which may link the monomer units together in the polymer structure.

As used herein, the term "nitrogen containing substituent" when used in reference to a substituent on the lignin backbone includes both quaternary ammonium cationic substituents and anime substituents (i.e., primary, secondary, and tertiary amine substituents) that may form ammonium cationic substituents after protonation, for example, protonation under at least mildly acidic conditions or conditions where the pKa of solution are less than the pKa of the amine.

As used herein, the term "cleaning composition" includes, but is not limited to, laundry cleaning compositions, laundry soap products, fabric care compositions, hard surface cleaning compositions, dish cleaning compositions, home care cleaning compositions, and personal care cleaning compositions, for example, for use in the health and beauty area.

Cleaning compositions include granular, powder, liquid (including heavy duty liquid ("HDL") detergents), gel, paste, bar form and/or flake type cleaning agents, laundry detergent cleaning agents, laundry soak or spray treatments and pre-treatments, fabric treatment compositions, dish washing detergents and soaps, shampoos, hand washing compositions, body washes and soaps, and other similar cleaning compositions. As used herein, the term "fabric treatment composition" includes, unless otherwise indicated, fabric softening compositions, fabric enhancing compositions, fabric freshening compositions and combinations thereof. Such compositions may be, but need not be wash or rinse added compositions.

As used herein, the term "personal care cleaning composition" includes shampoos, hand washing compositions, body washing compositions, hair removal compositions, bath soaps, bar soaps, bath beads, cosmetics, beauty bars, and lotions.

As used herein, the term "comprising" means various components conjointly employed in the preparation of the compositions or methods of the present disclosure. Accordingly, the terms "consisting essentially of" and "consisting of" are embodied in the term "comprising".

As used herein, the articles including "the", "a" and "an" when used in a claim or in the specification, are understood to mean one or more of what is claimed or described.

As used herein, the terms "include", "includes" and "including" are meant to be non-limiting.

As used herein, the term "plurality" means more than one.

As used herein, the terms "residue", "monomer residue" and "residue of a monomer" when used with reference to the structure of a polymer mean the chemical structure of the monomer unit remaining after the monomer unit has been incorporated into the polymer chain by the polymerization reaction.

As used herein, the terms "fabric", "textile", and "cloth" are used non-specifically and may refer to any type of material, including natural, artificial, and synthetic fibers, such as, but not limited to, cotton, wool, polyester, nylon, silk and the like, including blends of various fabrics or textiles.

As used herein, the terms "dispersant" and "dispersant polymer" mean that the composition provides dispersal and anti-redeposition benefits, thereby minimizing the amount of suspended soil or staining material that deposits on the cleaned surface, thus providing improved color and whiteness benefits. For example, although non-limiting, the dispersant may deposit onto the soil particles in solution and through stabilization of the soil particles in suspension, for example, by one or more of steric stabilization or ionic stabilization, prevent or minimize flocculation and redeposition of the soil or staining material onto the cleaned surface. For example, although not limiting to the disclosure, dispersants may bind to anionic surfaces of dislodged clay particles and form a stabilized suspension of the particles and hold the particles in solution until they are removed during the cleaning process thus preventing the particles from re-depositing upon the cleaned surface.

As used herein, the terms "suds boosting" or "suds stabilizing" includes polymers and compositions that can increase the level of suds or foam produced by the cleaning composition and/or increase the duration that the suds or foam last by stabilizing the bubbles in the suds or foam; compared to the suds or foam of a composition that does not contain the suds boosting and stabilizing composition.

As used herein, the term "soil release" means the composition or polymer assists in the release of soil from the surface of a soiled object, such as a textile fiber surface. This may include modification, binding to, or coating at least a portion of a textile fiber surface with the composition or polymer to at least partially decrease the binding affinity or strength of the soil, stain or grease/oil compositions that come in contact with the treated fabric surface, thereby aiding in the removal of the soil, stain or grease/oil from the fabric surface during the washing process. In addition, soil release includes release of soil absorbed into a textile fiber.

As used herein, the term "randomly substituted" means the substituents on the monomer residues in the randomly substituted polymer occur in a non-repeating or random fashion. That is, the substitution on a substituted monomer residue may be the same or different (i.e., substituents (which may be the same or different) on different atoms on the monomer residues) from the substitution on a second substituted monomer residue in a polymer, such that the overall substitution on the polymer has no pattern. Further, the substituted monomer residues occur randomly within the polymer (i.e., there is no pattern with the substituted and unsubstituted monomer residues within the polymer).

As used herein, the "substituent weight percentage" of a substituent group on lignin polymers is an average measure of the number of substituent groups on each monomeric unit which are derivatized by the substituent groups. For example, in lignin polymers each phenyl propyl unit may have up to three (or more) potential hydroxyl or methoxy groups available for substitution. However, for each monomer residue, the number of substitutable hydroxyl or methoxy groups may vary, for example, due to the source of the lignin, the source of the monomer residue (i.e., p-coumaryl alcohol, coniferyl alcohol or sinapyl alcohol), the amount of derivatization during the lignin formation or isolation process, and the placement of polymer linkages and cross-linkages within the monomer residue. Thus, substituent weight percentage expresses the quotient of the weight of all of the particular substituent groups divided by total weight of the polymer (substituents+backbone) times 100 (i.e., (R wt./polymer wt)× 100). There are number of ways to determine substituent weight percentage of modified lignin polymers described herein. The methods used will depend on the type of substituent on the biopolymer. For example, the substituent weight percentage can be determined using proton nuclear magnetic resonance spectroscopy ("$^1$H NMR") or other analytical methods that are well-known in the art.

As used herein, the term "average molecular weight" refers to the average molecular weight of the polymer chains in a polymer composition. Average molecular weight may be calculated as either the weight average molecular weight ("$M_w$") or the number average molecular weight ("$M_n$"). Weight average molecular weight may be calculated using the equation:

$$M_w = (\Sigma_i N_i M_i^2)/(\Sigma_i N_i M_i)$$

where $N_i$ is the number of molecules having molecular weight $M_i$. Number average molecular weight may be calculated using the equation:

$$M_n = (\Sigma_i N_i M_i)/(\Sigma_i N_i).$$

The weight and number average molecular weight may be measured according to gel permeation chromatography ("GPC"), size exclusion chromatography, or other analytical methods.

Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Modified Lignin Polymer Composition

The present disclosure provides for modified lignin polymer compositions. The modified lignin polymers may be used as a component in a cleaning composition and may provide certain benefits, such as, but not limited to, cleaning and dispersal benefits, soil release benefits, and suds boosting benefits. Further, methods of forming cleaning compositions and of treating a substrate are also described.

Lignin is a complex oligomer or polymer commonly derived from wood and is an integral part of the cell walls of plants. Lignin is of interest as a primary byproduct of the pulp industry, where it must be removed prior to the production of paper products. Lignin is also produced as a byproduct of other industries which involve the manipulation of plant material. It is produced in large quantities and is relatively inexpensive, so its use as a raw material in consumer compositions and products is of particular interest.

Figure 2:
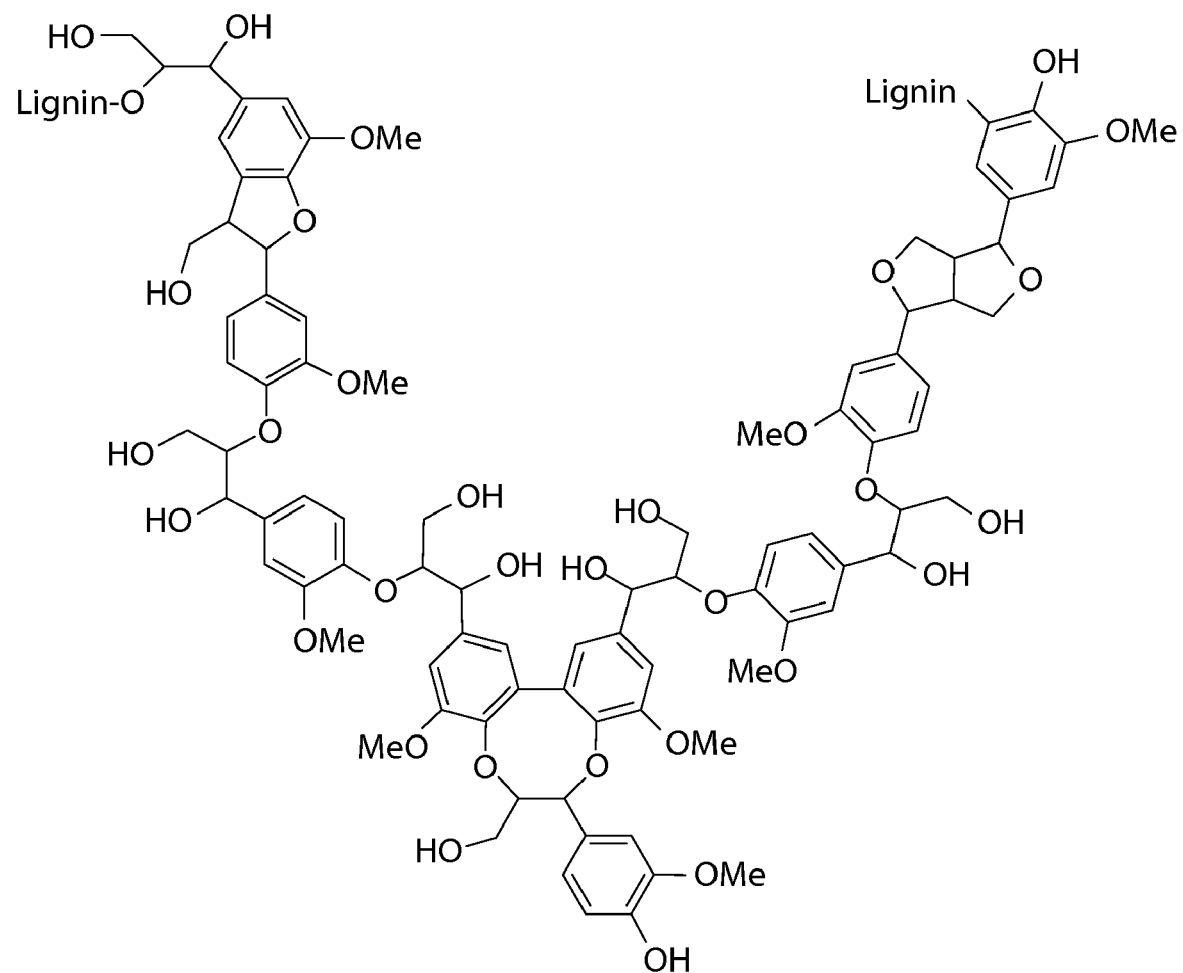

The lignin molecular structure is complex and random, comprising substituted phenylpropane monomers polymerized in a seemingly random and unorganized fashion and having a plurality of hydroxyl and methoxyl substituents. FIGS. 1 and 2 provide exemplary illustrations of two lignin structures. It is believed that the lignin polymeric structure arises from radical coupling reactions between three primary monomers, the monolignols: p-coumaryl alcohol, coniferyl alcohol, and sinapyl alcohol. This lignification process produces a polydisperse polymer with no extended sequences of regularly repeating units, with a composition generally characterized by the relative abundance of p-hydroxylphenyl, guiacyl, and syringyl units and by the distribution of inter-unit linkages in the polymer (see FIGS. 1 and 2).

The distribution of these monolignol units in the lignin polymer structure depends at least in part on the lignin source since lignins differ from plant species to species, and even from one tissue to the next in the same plant or within the plant cell itself. Further, lignin structure may differ according to the physical and chemical manipulations used during the isolation of the lignin from the source material.

A variety of industrial isolation methods have been used for extraction of the lignin from the source material. The lignins produced upon isolation include lignin sulfonates, Kraft lignins, soda lignins, organosolve lignins, steam explosion lignins, softwood lignin, hardwood lignin, cellulosic grasses lignins, corn stover lignins, and other lignins, all of which may be suitably modified to produce the modified lignin compositions of the present disclosure.

The modified lignin polymers of the present disclosure have been modified to include at least two substituents selected from nitrogen containing substituents, anionic substituents, and alkoxy substituents. Nitrogen containing substituents include substituents having at least one quaternary ammonium cation or at least one amine nitrogen (i.e., primary, secondary or tertiary amine) which may be protonated under mildly acidic conditions to form an ammonium cation. According to these embodiments, the modified lignin polymer include substitution patterns such as, lignin backbones comprising both anionic substituents and nitrogen containing substituents; lignin backbones comprising both anionic substituents and alkoxy substituents; lignin backbones comprising both nitrogen containing substituents and alkoxy substituents; and lignin backbones comprising anionic substituents, nitrogen containing substituents, and alkoxy substituents. The lignin backbone may be modified by derivatizing two or more of the hydroxy groups on the backbone with at least two of an anionic substituent, a nitrogen containing substituent, and/or an alkoxy substituent. This derivatization includes replacing the hydrogen of the hydroxy group with the substituent group to form an ether linkage between the lignin backbone and the substituent (i.e., a structure R—O—B, were R is the substituent and B is the lignin backbone). In other embodiments, a methoxy substituent on the lignin polymer backbone may be reacted to form an anionic substituent, a nitrogen containing substituent, and/or an alkoxy substituent (i.e., replace the methyl of the methoxy group with the substituent group). Alternatively, the lignin backbone may be modified by an aromatic substitution-type reaction to attach an anionic substituent, a nitrogen containing substituent, or an alkoxy substituent to a carbon of one or more of the phenyl rings in the lignin structure (i.e., replace a hydroxy, a methoxy or an aromatic hydrogen with the substituent group). Other chemical methods known to those of ordinary skill in the art for modifying the lignin structure (such as at a hydroxy group, methoxy group, or aromatic carbon) by derivatizing the lignin backbone with two of more anionic substituents, nitrogen containing substituents, and alkoxy substituents are also contemplated.

According to certain embodiments, the present disclosure provides for modified lignin polymers. The modified lignin polymer may comprise a randomly substituted lignin backbone comprising substituted lignin monomer residues and unsubstituted lignin monomer residues, wherein at least two or more of the hydroxyl groups, methoxy groups, or aromatic carbons on the randomly substituted lignin backbone have been substituted with R substituent groups. Each R substituent group may be independently selected from R substituent types comprising a nitrogen containing substituent $R^1$ with a substitution weight percentage ranging from 0% to 75%, an anionic substituent $R^2$ with a substitution weight percentage ranging from 0% to 90%, an alkoxy substituent $R^3$ with a substitution weight percentage ranging from 0% to 90%, and combinations of any thereof, provided that the randomly substituted lignin backbone comprises at least two different R substituent types. As discussed herein, the randomly substituted lignin backbone may have a substitution pattern including both anionic substituents $R^2$ and nitrogen containing substituents $R^1$; both anionic substituents $R^2$ and alkoxy substituents $R^3$; both nitrogen containing substituents $R^2$1 and alkoxy substituents $R^3$; and all three of anionic substituents $R^2$, nitrogen containing substituents $R^1$, and alkoxy substituents $R^3$.

Other embodiments of the present disclosure provide for modified lignin polymers comprising a randomly substituted lignin backbone having a structure represented by Formula I:

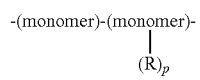

I which comprises substituted lignin monomer residues and unsubstituted lignin monomer residues selected from the group consisting of substituted and unsubstituted residues of p-coumaryl alcohol, substituted and unsubstituted residues of coniferyl alcohol, substituted and unsubstituted residues of sinapyl alcohol, derivatives of the substituted and unsubstituted residues, and mixtures thereof. The residues of the substituted monomer may comprise —$(R)_p$ substituent groups, where p is an integer from 1 to 3. That is, at least one, and in specific embodiments a plurality of the residues of the substituted lignins monomers may be substituted monomer residues having 1, 2, or 3 substituent groups R attached to the substituted monomer residue. In specific embodiments, at least two or more of the hydroxyl, methoxy, or aromatic carbons of the randomly substituted lignin backbone may be substituted with R substituent groups. Each R substituent group may be independently selected from R substituent types comprising a nitrogen containing substituent $R^1$ with a substitution weight percentage ranging from 0% to 75%, an anionic substituent $R^2$ with a substitution weight percentage ranging from 0% to 90%, an alkoxy substituent $R^3$ with a substitution weight percentage ranging from 0% to 90%, and combinations of any thereof, provided that the randomly substituted lignin backbone comprises at least two different R substituent types. Certain embodiments of the modified lignin polymer may further comprise hydrophobic substituents. Examples of structures for the nitrogen containing substituents, the anionic substituents, the alkoxy substituents, and the hydrophobic substituents are set forth herein.

Lignins suitable for modification to produce the modified lignin polymer according to the various embodiments herein include, but are not limited to, lignin sulfonates, Kraft lignins, soda lignins, organosolv lignins, softwood lignin, hardwood lignin, cellulosic grasses lignins, corn stover lignins, steam explosion lignins, and combinations of any thereof. As discussed herein, the lignin polymer structure depends at least in part on the lignin source and/or isolation process. However, lignin polymer structure, regardless of source or isolation process, comprises a plurality of at least hydroxyl, methoxyl, and/or aromatic carbons, which may be reacted to form the desired substitution patterns of the compositions of the present disclosure. Thus, lignins from any source may be used herein. The lignins may be directly derivatized to randomly substitute the lignin backbone with two or more types of the substituents disclosed herein.

According to certain embodiments, the modified lignin polymer may have a weight average molecular weight ranging from 2,000 Daltons to 300,000 Daltons. In other embodiments, the modified lignin polymer may have a weight average molecular weight ranging from 5,000 Daltons to 300,000 Daltons, or 2,000 Daltons to 100,000 Daltons, or even 3,000 Daltons to 50,000 Daltons. The weight average molecular weight of the modified lignin polymers of the present disclosure will depend on the molecular weight, degree of polymerization, and complexity of the lignin backbone, as well as the substitution weight percentage and weight of the various substituents added to the lignin backbone. For example, in certain embodiments, the lignin backbone may have a relatively low molecular weight with a high amount of substitution. Alternatively, in other embodiments, the lignin backbone may have a relatively high molecular weight while having a relatively low amount of substitution. Both of these embodiments may have approximately the same overall weight average molecular weight and may demonstrate the desired cleaning benefits discussed herein.

According to various embodiments, the lignin may be modified directly after isolation. For example, the lignin may be modified without any intermediate treatment, such as a degradation of the lignin structure to produce lignin phenols. Lignin phenols are the degradation product having molecular weights of less than 1,500 Daltons which are produced when lignin is treated with harsh hydrolysis conditions. However, the inventors of the present disclosure, while not intending to be limited, believe that modified lignin polymers having a weight average molecular weights ranging from at least 2,000 Daltons up to 300,000 Daltons provide desired benefits, for example the desired cleaning benefits. Further, it is an industrial and economic advantage to modify the lignins directly after isolation and without any intermediate treatment or degradation process, thus producing the desired substance without additional intermediate processing or transformations.

As discussed herein, in certain embodiments, it may be desirable to vary the number of substituents (as measured by their substitution weight percentage) according to the molecular weight of the lignin being modified. For example, the inventors have found that products formed with low molecular weight lignin starting materials (i.e., lignins having a weight average molecular weight ranging from 2,000 Daltons to 10,000 Daltons) perform better in cleaning compositions when the lignin backbone has a high percentage of substitution (i.e., substitution weight percentages ranging from 10% to 90%). Alternatively, embodiments comprising products formed with high molecular weight lignin starting materials (i.e., lignins having a weight average molecular weight ranging from 25,000 Daltons to 150,000 Daltons) perform better in cleaning compositions when the lignin backbone has a low percentage of substitution (i.e., substitution weight percentages ranging from 0.01% to 10%). This link between lignin molecular weight and substitution weight percentage may be due, at least in part, because cleaning compositions comprising the modified lignin polymers may have more preferred adsorptive properties, peptization properties, dispersion properties, emulsification properties, and/or lowered surface tensions when the low molecular weight lignin has a high substitution weight percentage or when the high molecular weight lignin has a low substitution weight percentage.

According to specific embodiments, the randomly substituted lignin backbones that form the modified lignin polymers comprise substituted lignin monomer residues and unsubstituted lignin monomer residues. As discussed herein, the randomly substituted lignin backbone comprises substituted and unsubstituted lignin monomer residues selected from substituted and unsubstituted residues of p-coumaryl alcohol, substituted and unsubstituted residues of coniferyl alcohol, substituted and unsubstituted residues of sinapyl alcohol, derivatives of these substituted and unsubstituted residues, and mixtures thereof. As will be understood by one in the art, the lignin backbone will contain different amounts of each of the substituted and unsubstituted monomer residues and may comprise other components depending on the source and isolation process. Further, the substitution pattern on each of the monomer residues may differ within the polymer structure from other similar residues depending, at least in part, on the structure and conformation of the polymer backbone structure and/or the random cross-linking patterns among the monomer residues in the polymer structure. According to certain embodiments, each R substituent may be attached to the lignin backbone at an oxygen on the lignin backbone. For example, the R substituent may be attached to the lignin backbone at a site that had a hydroxyl substitution on the backbone or a site that had a methoxyl substitution on the backbone. In other embodiments, the R substituent may be attached directly to the lignin backbone at an aromatic carbon atom (i.e., a carbon atom in a phenyl ring).

As recited herein, the modified lignin polymers of the present disclosure may comprise one or more nitrogen containing substituents $R^1$ with a substitution weight percentage ranging from 0% to 75%. In certain embodiments the nitrogen containing substituents $R^1$ may have a substitution weight percentage ranging from 0.01% to 30%, or even from 2% to 10%. Certain embodiments of the modified lignin polymers will contain a plurality of nitrogen containing substituents $R^1$. According to specific embodiments, each nitrogen containing substituent $R^1$ may independently have a structure according to Formula II:

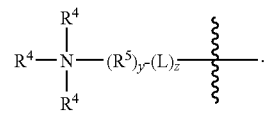

II

Referring to Formula II, according to these embodiments, each $R^4$ is a substituent group selected from a lone pair of electrons; H; $CH_3$; or a linear or branched, saturated or unsaturated $C_2$-$C_{18}$ alkyl. According to certain embodiments of the $R^1$ nitrogen containing group, two or more of the $R^4$ groups of Formula II must not be a lone pair of electrons. That is, in these embodiments, one $R^4$ group may be a lone pair of electrons such that the nitrogen containing end group in Formula II is an amine group (i.e., a primary, secondary, or tertiary amine group) under neutral or basic conditions. It will be understood by one skilled in the art that the amine group according to this embodiment may be protonated under mildly acidic conditions or specific pKa conditions to provide a cationic charged ammonium ion. According to other embodiments of the $R^1$ nitrogen containing group, no $R^4$ group in Formula II is a lone pair of electrons, such that the nitrogen containing end group in Formula II is a positively charged quaternary ammonium cation. Referring still to Formula II, $R^5$ may be a linear or branched, saturated or unsaturated $C_2$-$C_{18}$ alkyl chain or a linear or branched, saturated or unsaturated secondary hydroxy($C_2$-$C_{18}$)alkyl chain. In various embodiments, the group L is a linking group selected from —O—, —C(=O)O—, —OC(=O)—, —$NR^6$—, —C(=O)$NR^6$—, —$NR^6$C(=O)—, and —$NR^6$C(=O)$NR^6$—, where $R^6$ is H, or $C_1$-$C_6$ alkyl. According to the various embodiments, y may have a value of 0 or 1, and z may have a value of 0 or 1.

As recited herein, the modified lignin polymers of the present disclosure may comprise one or more anionic substituents $R^2$ with a substitution weight percentage ranging from 0% to 90%. In certain embodiments the anionic substituents $R^2$ may have a substitution weight percentage ranging from 1% to 90%, or 1% to 40%, or even from 4% to 30%. Certain embodiments of the modified lignin polymers will contain a plurality of anionic substituents $R^2$. According to specific embodiments, each anionic substituent $R^2$ may independently have a structure according to Formula III:

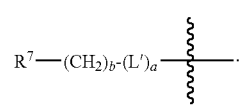

III

According to these embodiments, each $R^7$ may be an anionic substituent selected from a carboxylate (—$COO^-$), carboxymethyl (—$CH_2COO^-$), succinate (—$OOCCH_2CH_2COO^-$), sulfate (—$OS(O_2)O^-$), sulfonate (—$S(O_2)O^-$), arylsulfonate (—Ar—$S(O_2)O^-$, where Ar is an aryl ring), phosphate (—OPO$_2$(OR')$^-$ or —OPO$_3^{2-}$, where R' is a H, alkyl, or aryl), phosphonate (—PO$_2$(OR')$^-$ or PO$_3^{2-}$, where R' is a H, alkyl, or aryl), dicarboxylate (—Y(COO$^-$)$_2$, where Y is alkyl or aryl), or polycarboxylate (—Y(COO$^-$)$_t$, where Y is alkyl or aryl and t is greater than 2). In various embodiments, the group L' is a linking group selected from —O—, —C(=O)O—, —OC(=O)—, —NR$^8$—, —C(=O)NR$^8$—, —NR$^8$C(=O)—, and —NR$^8$C(=O)NR$^8$—, where R$^8$ is H, or C$_1$-C$_6$ alkyl. According to the various embodiments, a may have a value of 0 or 1, and b is an integer having a value from 0 to 18.

As recited herein, the modified lignin polymers of the present disclosure may comprise one or more alkoxy substituents R$^3$ with a substitution weight percentage ranging from 0% to 90%. In certain embodiments the alkoxy substituents R$^3$ may have a substitution weight percentage ranging from 5% to 90%, or even from 10% to 80%. Certain embodiments of the modified lignin polymers will contain a plurality of alkoxy substituents R$^3$. According to specific embodiments, each alkoxy substituent R$^3$ may independently have a structure according to Formula IV:

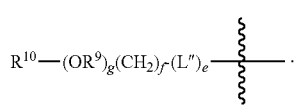

IV

According to these embodiments, each R$^9$ may be a group selected from ethylene, propylene, butylene, or mixtures thereof. In certain embodiments, the structure of (OR$^9$) may be a polyethylene oxide group, a polypropylene oxide group, a polybutylene oxide group or mixtures thereof. In specific embodiments, R$^9$ may have a structure —CH(R$^{12}$)CH$_2$—, where each R$^{12}$ is independently chosen from hydrogen, methyl or ethyl (i.e., polyethylene oxide, polypropylene oxide and polybutylene oxide, respectively). The structure "OR$^9$" includes structures where an oxygen is between R$^9$ and R$^{10}$ and structures where an oxygen is between R$^9$ and (CH$_2$)$_f$. Each R$^{10}$ group may be an end group selected from hydrogen, C$_1$-C$_{20}$ alkyl (which may be branched or unbranched, and saturated or unsaturated), hydroxy, —OR$^1$, or —OR$^2$ (where R$^1$ and R$^2$ are as described herein). In various embodiments, the group L" is a linking group selected from —O—, —C(=O)O—, —OC(=O)—, —NR$^{11}$—, —C(=O)NR$^{11}$—, —NR$^{11}$C(=O)—, and NR$^{11}$C(=O)NR$^{11}$—, where R$^{11}$ is H, or C$_1$-C$_6$ alkyl. According to the various embodiments, e may have a value of 0 or 1, f is an integer having a value from 0 to 8, and g is an integer having a value from 0 to 50.

According to other embodiments, the modified lignin polymers may further comprise one or more hydrophobic substituents R$^{13}$ attached to the lignin backbone at an oxygen substitution or a carbon atom on the backbone, for example at an oxygen where a hydroxyl substituent or methoxy substituent was or at an aromatic carbon atom. Hydrophobic substituents R$^{13}$ on the lignin backbone according to these embodiments may have a substitution weight percentage ranging from 0.1% to 50%. In other embodiments, the hydrophobic substituents may have a substitution weight percentage ranging from 1% to 30%, or even from 5% to 20%. Each hydrophobic substituent R$^{13}$ may independently have a structure selected from a linear or branched, saturated or unsaturated C$_1$-C$_{18}$ alkyl, a linear or branched, saturated or unsaturated C$_7$-C$_{18}$ alkylaryl, a linear or branched, saturated or unsaturated secondary hydroxy(C$_2$-C$_{18}$)alkyl, or a hydrophobic polymer graft. Hydrophobic substituent R$^{13}$ may also comprise linear or branched, saturated or unsaturated C$_1$-C$_{18}$ alkyl ethers. Addition of one or more hydrophobic substituents may improve certain desired characteristics of the modified lignin polymers, such as, but not limited to, reduction of interfacial tensions improved dispersancy and improved deposition characteristics of the polymer in aqueous systems, such as fabric care systems.

Cleaning Compositions

According to certain embodiments, the modified lignin polymers of the present disclosure may be incorporated into a cleaning composition, such as, but not limited to, a fabric care composition, a dish cleaning composition, a home care composition or a personal care composition. Examples of cleaning compositions include, but are not limited to, liquid laundry detergents, solid laundry detergents, laundry soap products, laundry spray treatment products, laundry pretreatment products, hand dish washing detergents, automatic dishwashing detergents, a beauty care detergent, hard surface cleaning detergents, carpet cleaning detergents, a shampoo, and a household cleaning detergent. Examples of fabric care compositions suitable for the present disclosure include, but are not limited to, liquid laundry detergents, heavy duty liquid laundry detergents, solid laundry detergents, laundry soap products, laundry spray treatment products, laundry pretreatment products, laundry soak products, heavy duty liquid detergents, and rinse additives. Examples of suitable dish cleaning compositions include, but are not limited to, automatic dishwasher detergents, detergents for hand washing of dishes, liquid dish soap, and solid granular dish soap. Examples of suitable home care compositions include, but are not limited to, rug or carpet cleaning compositions, hard surface cleaning detergents, floor cleaning compositions, window cleaning compositions, toilet and bathroom cleaning compositions, household cleaning detergents, and car washing detergents. Examples of suitable personal care compositions include, but are not limited to, beauty care detergents, beauty bars, bar soap, bath beads, bath soaps, hand washing compositions, body washes and soaps, shampoo, conditioners, cosmetics, hair removal compositions, and oral care compositions.

Certain embodiments of the present disclosure provide cleaning compositions, such as, but not limited to, those described herein. The cleaning compositions may comprise a modified lignin polymer having a randomly substituted lignin backbone, such as any of the modified lignin structures described herein. For example, the substituted lignin backbone may comprise substituted lignin monomer residues and unsubstituted lignin monomer residues wherein at least two or more of the hydroxyl, methoxy, and/or aromatic carbons on the randomly substituted lignin backbone have been substituted with R substituent groups. Descriptions and structures for the R substituent groups (or R substituent types) on the randomly substituted lignin backbone are set forth herein. According to the various embodiments, the randomly substituted lignin backbone comprises at least two different R substituent types.

In various embodiments, the cleaning compositions described herein may further comprise at least one or more adjunct. Suitable adjuncts include, but are not limited to, bleach activators, surfactants, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, perfumes, perfume delivery systems, structure elasticizing agents, fabric softeners, carriers, hydrotropes, processing aids, and pigments. Certain adjuncts are described in detail elsewhere herein. The cleaning compositions may be any cleaning composition product listed herein including, but not limited to, fabric care compositions, liquid laundry detergents, solid laundry detergents, laundry soap products, laundry spray treatment products, laundry pre-treatment products, hand dish washing detergents, automatic dishwashing detergents, a beauty care detergent, hard surface cleaning detergents, carpet cleaning detergents, a shampoo, and a household cleaning detergent.

The various embodiments of the cleaning compositions comprising the modified lignin polymers described herein may show improved cleaning characteristics and benefits compared to cleaning compositions that do not comprise the modified lignin polymers. For example, according to certain embodiments, the cleaning compositions comprising the modified lignin polymer may demonstrate one or more of improved dispersion and anti-redeposition characteristics and benefits, improved suds boosting and stabilization characteristics and benefits, and improved soil release characteristics and benefits, compared to cleaning compositions that do not comprise the modified lignin polymers.

When cleaning a substrate, such as, but not limited to, a fabric or a hard surface, a cleaning composition must effectively solubilize any oil, grease dirt, soil, or other staining material on the substrate, that is the composition must disperse the oil, grease dirt, soil, or other staining material from the surface of the substrate material into the solution comprising the cleaning composition. Further, once solubilized or dispersed into the solution comprising the cleaning composition, an effective cleaning composition must then prevent the solubilized oil, grease dirt, soil, or other staining material from redepositing onto the surface of the substrate or, in certain embodiments, any other surface in the cleaning environment. According to these embodiments, the solubilized or dispersed oil, grease dirt, soil, or other staining material may then be disposed of, for example, by rinsing away and/or washing down a drain. Various embodiments of the cleaning compositions comprising the modified lignin polymers of the present disclosure may show improved soil dispersion and anti-redeposition benefits over cleaning compositions which do not comprise the modified lignin polymers.

Further when cleaning a substrate, suds may be viewed by such consumers as an important signal that the cleaning composition is "working" and is an active driver of accomplishing their cleaning objectives. Thus, rapidly generated high volumes of suds and well retained suds during the washing cycle are highly preferred. On the other hand, a high volume of suds in the washing cycle typically results in suds being carried over to the rinse bath solution and requiring additional time, energy and water to thoroughly rinse the laundered or cleaned items. Accordingly, quick collapse of suds in rinsing solution is another preferred aspect of the sudsing profile of a cleaning/detergent composition. However, widely used high suds detergents in the art typically comprises a high level of surfactant and builder, such as more than 15% of surfactant and more than 10% of builder. Recently, the impact of excessive use of such raw materials and their impact on the environment has become a concern as such materials exhaust non-renewable natural resources and may ultimately be discharged into the environment, such as into rivers and lakes. Further, there is a need to minimize the use of petrochemical based materials and increase the use renewable and biodegradable materials to improve the environmental impact of detergent chemicals. Thus, compositions that can boost and/or stabilize the suds developed during the cleaning process may be desirable on both an aesthetic level and an economic level. Various embodiments of the cleaning compositions comprising the modified lignin polymers of the present disclosure may provide a desired suds profile, i.e., improved suds formation and suds stabilization, compared to cleaning compositions that do not comprise the modified lignin polymers.

In addition, cleaning of a surface, for example a fabric fiber surface may benefit from improved soil release properties. This may include modification, binding to, or coating at least a portion of a textile fiber surface with the composition or polymer to at least partially decrease the binding affinity or strength of the soil, stain or grease/oil compositions to the fabric surface, thereby aiding in the removal of the soil, stain or grease/oil from the treated fabric surface during the washing process. Improved soil release properties of the cleaning composition may allow for reduced addition of other cleaning elements such as surfactants, peptizing polymers and builders, thereby providing economic savings. According to certain embodiments, the modified lignin polymers described herein may act as effective soil release polymers that may deposit on, bind to, or coat at least a portion of a textile fiber surface treated with a cleaning composition comprising the modified lignin polymer, and at least partially decrease the binding affinity or strength of the soil, stain or grease/oil compositions to the treated fabric surface, thereby aiding in the removal of the soil, stain or grease/oil from the fabric surface during a washing process and subsequent washing processes. Thus, the cleaning compositions comprising the modified lignin polymers of the various embodiments herein may display improved soil release characteristics and benefits compared to cleaning compositions that do not comprise the modified lignin polymers.

Still other embodiments of the present disclosure provide methods for making a cleaning composition, such as those described herein. According to these embodiments, the methods for making the cleaning compositions comprise adding the modified lignin polymer to the cleaning composition. According to these embodiments of the methods, the modified lignin polymers may be any modified lignin polymer having a randomly substituted lignin backbone according to the various embodiments described herein. For example, the randomly substituted lignin backbone may comprise substituted lignin monomer residues and unsubstituted lignin monomer residues as set forth herein. According to these embodiments, at least two or more of the hydroxyl groups, the methoxy groups or aromatic carbon atoms on the randomly substituted lignin backbone have been substituted with R substituents, as described in detail herein, provided that the randomly substituted lignin backbone comprises at least two different R substituent types. For example, each R substituent group may be independently an R substituent type selected from the group consisting of nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%.

According to specific embodiments, the methods may further comprise adding at least one or more adjuncts to the cleaning composition. Suitable adjuncts include, but are not limited to, bleach activators, surfactants, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, perfumes, perfume delivery systems, structure elasticizing agents, fabric softeners, carriers, hydrotropes, processing aids, and pigments, as described herein.

In other embodiments, the methods may further comprise modifying a lignin polymer, such as, but not limited to lignin sulfonates, Kraft lignins, soda lignins, organosolv lignins, softwood lignin, hardwood lignin, steam explosion lignins, cellulosic grasses lignins, corn stover lignins, and combinations of any thereof. Modifying the lignin polymer may include substituting at least two hydroxyl groups on a lignin polymer backbone with at least two R substituent groups, as described herein. In other embodiments, modifying the lignin polymer may include substituting at least two of the hydroxy, methoxy or aromatic carbons on the lignin polymer backbone with at least two R substituent groups.

Still further embodiments of the present disclosure provide methods of treating a substrate comprising contacting the substrate with an effective amount of a cleaning composition comprising the modified lignin polymer according to the various embodiments disclosed herein. Suitable substrates include fabric and textiles, hard and soft surfaces, dishes, hair, skin, and teeth.

Suitable examples of fabrics include, but are not limited to, natural fabrics such as cottons, bamboo fabrics, wool fabrics and other fabrics derived from animal fur, silks, linens, and hemp fabrics; and artificial and synthetic fabrics such as polyester fabrics, nylon fabrics, acetate fabrics, rayon fabrics, acrylic fabrics, and olefin fabrics, as well as blends of the various natural fibers, artificial fibers and/or synthetic fibers. Examples of fabric care compositions include, but are not limited to, laundry detergent cleaning agents, laundry soak or spray treatments, fabric treatment compositions, liquid laundry detergents, solid laundry detergents, laundry soap products, laundry spray treatment products, heavy duty liquid detergents, and rinse additives. Contacting the fabric may be as a pre-treatment or contacting during a cleaning process, such as, during a wash cycle or rinse cycle.

In those aspects of the cleaning composition where the composition is a fabric care composition, the fabric care compositions may take the form of liquid, laundry detergent compositions. In one aspect, such compositions may be a heavy duty liquid (HDL) composition. Such compositions may comprise a sufficient amount of a surfactant to provide the desired level of one or more cleaning properties, typically by weight of the total composition, from about 5% to about 90%, from about 5% to about 70% or even from about 5% to about 40% and the modified lignin polymer of the present disclosure, to provide a soil and/or stain removal benefit to fabric washed in a solution containing the detergent. Typically, the detergent is used in the wash solution at a level of from about 0.0001% to about 0.05%, or even from about 0.001% to about 0.01% by weight of the wash solution.

The cleaning compositions may additionally comprise an aqueous, non-surface active liquid carrier. Generally, the amount of the aqueous, non-surface active liquid carrier employed in the compositions herein will be effective to solubilize, suspend or disperse the composition components. For example, the compositions may comprise, by weight, from about 5% to about 90%, from about 10% to about 70%, or even from about 20% to about 70% of an aqueous, non-surface active liquid carrier.

The most cost effective type of aqueous, non-surface active liquid carrier may be water. Accordingly, the aqueous, non-surface active liquid carrier component may be generally mostly, if not completely, water. While other types of water-miscible liquids, such alkanols, diols, other polyols, ethers, amines, and the like, may be conventionally added to cleaning compositions as co-solvents or stabilizers, in certain embodiments of the present disclosure, the utilization of such water-miscible liquids may be minimized to hold down composition cost. Accordingly, in certain embodiments, the aqueous liquid carrier component of the liquid detergent products herein will generally comprise water present in concentrations ranging from about 5% to about 90%, or even from about 20% to about 70%, by weight of the composition.

The cleaning compositions herein, such as, but limited to liquid detergent compositions, may take the form of an aqueous solution or uniform dispersion or suspension of surfactant, modified lignin polymer, and certain optional adjunct ingredients, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable and will typically have a viscosity which ranges from about 100 to 600 cps, more preferably from about 150 to 400 cps. For purposes of this disclosure, viscosity may be measured with a Brookfield LVDV-II+ viscometer apparatus using a #21 spindle. Suitable surfactants may be anionic, nonionic, cationic, zwitterionic and/or amphoteric surfactants. In one embodiment, the cleaning composition comprises anionic surfactant, nonionic surfactant, or mixtures thereof.

Suitable anionic surfactants may be any of the conventional anionic surfactant types typically used in cleaning compositions, such as liquid or solid detergent products. Such surfactants include the alkyl benzene sulfonic acids and their salts as well as alkoxylated or non-alkoxylated alkyl sulfate materials. Exemplary anionic surfactants are the alkali metal salts of $C_{10}$-$C_{16}$ alkyl benzene sulfonic acids, preferably $C_{11}$-$C_{14}$ alkyl benzene sulfonic acids. In one aspect, the alkyl group is linear. Such linear alkyl benzene sulfonates are known as "LAS". Such surfactants and their preparation are described for example in U.S. Pat. Nos. 2,220,099 and 2,477,383. Especially preferred are the sodium and potassium linear straight chain alkylbenzene sulfonates in which the average number of carbon atoms in the alkyl group is from about 11 to 14. Sodium $C_{11}$-$C_{14}$, e.g., $C_{12}$ LAS is a specific example of such surfactants.

Another exemplary type of anionic surfactant comprises ethoxylated alkyl sulfate surfactants. Such materials, also known as alkyl ether sulfates or alkyl polyethoxylate sulfates, are those which correspond to the formula: R'—O—$(C_2H_4O)_n$—$SO_3M$ wherein R' is a $C_8$-$C_{20}$ alkyl group, n is from about 1 to 20, and M is a salt-forming cation. In a specific embodiment, R' is $C_{10}$-$C_{18}$ alkyl, n is from about 1 to 15, and M is sodium, potassium, ammonium, alkylammonium, or alkanolammonium. In more specific embodiments, R' is a $C_{12}$-$C_{16}$, n is from about 1 to 6, and M is sodium.

The alkyl ether sulfates will generally be used in the form of mixtures comprising varying R' chain lengths and varying degrees of ethoxylation. Frequently such mixtures will inevitably also contain some non-ethoxylated alkyl sulfate materials, i.e., surfactants of the above ethoxylated alkyl sulfate formula wherein n=0. Non-ethoxylated alkyl sulfates may also be added separately to the cleaning compositions of this disclosure and used as or in any anionic surfactant component which may be present. Specific examples of non-alkoxylated, e.g., non-ethoxylated, alkyl ether sulfate surfactants are those produced by the sulfation of higher $C_8$-$C_{20}$ fatty alcohols. Conventional primary alkyl sulfate surfactants have the general formula: $R''OSO_3^-M^+$ wherein R'' is typically a linear $C_8$-$C_{20}$ hydrocarbyl group, which may be straight chain or branched chain, and M is a water-solubilizing cation. In specific embodiments, R'' is a $C_{10}$-$C_{15}$ alkyl, and M is alkali metal, more specifically R'' is $C_{12}$-$C_{14}$ and M is sodium.

Specific, nonlimiting examples of anionic surfactants useful herein include: a) $C_{11}$-$C_{18}$ alkyl benzene sulfonates (LAS); b) $C_{10}$-$C_{20}$ primary, branched-chain and random alkyl sulfates (AS); c) $C_{10}$-$C_{18}$ secondary (2,3)-alkyl sulfates having Formulae (V) and (VI):

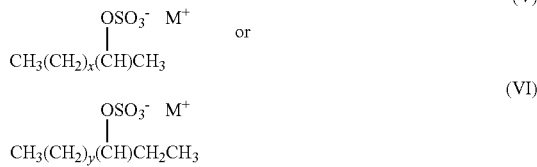

wherein M in Formulae (V) and (VI) is hydrogen or a cation which provides charge neutrality, and all M units, whether associated with a surfactant or adjunct ingredient, can either be a hydrogen atom or a cation depending upon the form isolated by the artisan or the relative pH of the system wherein the compound is used, with non-limiting examples of preferred cations including sodium, potassium, ammonium, and mixtures thereof, and x in Formula V is an integer of at least about 7, preferably at least about 9, and y in Formula VI is an integer of at least 8, preferably at least about 9; d) $C_{10}$-$C_{18}$ alkyl alkoxy sulfates ($AE_xS$) wherein preferably x in Formula V is from 1-30; e) $C_{10}$-$C_{18}$ alkyl alkoxy carboxylates preferably comprising 1-5 ethoxy units; f) mid-chain branched alkyl sulfates as discussed in U.S. Pat. Nos. 6,020,303 and 6,060,443; g) mid-chain branched alkyl alkoxy sulfates as discussed in U.S. Pat. Nos. 6,008,181 and 6,020,303; h) modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548.; i) methyl ester sulfonate (MES); and j) alpha-olefin sulfonate (AOS).

Suitable nonionic surfactants useful herein can comprise any of the conventional nonionic surfactant types typically used in liquid detergent products. These include alkoxylated fatty alcohols and amine oxide surfactants. Preferred for use in the liquid detergent products herein are those nonionic surfactants which are normally liquid. Suitable nonionic surfactants for use herein include the alcohol alkoxylate nonionic surfactants. Alcohol alkoxylates are materials which correspond to the general formula: $R^7(C_mH_{2m}O)_nOH$ wherein $R^7$ is a $C_8$-$C_{16}$ alkyl group, m is from 2 to 4, and n ranges from about 2 to 12. Preferably $R^7$ is an alkyl group, which may be primary or secondary, that contains from about 9 to 15 carbon atoms, more preferably from about 10 to 14 carbon atoms. In one embodiment, the alkoxylated fatty alcohols will also be ethoxylated materials that contain from about 2 to 12 ethylene oxide moieties per molecule, more preferably from about 3 to 10 ethylene oxide moieties per molecule. The alkoxylated fatty alcohol materials useful in the liquid detergent compositions herein will frequently have a hydrophilic-lipophilic balance (HLB) which ranges from about 3 to 17. More preferably, the HLB of this material will range from about 6 to 15, most preferably from about 8 to 15. Alkoxylated fatty alcohol nonionic surfactants have been marketed under the tradename NEODOL® by the Shell Chemical Company.

Another suitable type of nonionic surfactant useful herein comprises the amine oxide surfactants. Amine oxides are materials which are often referred to in the art as "semi-polar" nonionics. Amine oxides have the formula: $R'''(EO)_x(PO)_y(BO)_zN(O)(CH_2R')_2 \cdot qH_2O$. In this formula, R''' is a relatively long-chain hydrocarbyl moiety which can be saturated or unsaturated, linear or branched, and can contain from 8 to 20, preferably from 10 to 16 carbon atoms, and is more preferably $C_{12}$-$C_{16}$ primary alkyl. R' is a short-chain moiety, preferably selected from hydrogen, methyl and —$CH_2OH$. When x+y+z is different from 0, EO is ethyleneoxy, PO is propyleneoxy and BO is butyleneoxy. Amine oxide surfactants are illustrated by $C_{12}$-$C_{14}$ alkyldimethyl amine oxide.

Non-limiting examples of nonionic surfactants include: a) $C_{12}$-$C_{18}$ alkyl ethoxylates, such as, NEODOL® nonionic surfactants; b) $C_6$-$C_{12}$ alkyl phenol alkoxylates wherein the alkoxylate units are a mixture of ethyleneoxy and propyleneoxy units; c) $C_{12}$-$C_{18}$ alcohol and $C_6$-$C_{12}$ alkyl phenol condensates with ethylene oxide/propylene oxide block polymers such as PLURONIC® from BASF; d) $C_{14}$-$C_{22}$ mid-chain branched alcohols, BA, as discussed in U.S. Pat. No. 6,150,322; e) $C_{14}$-$C_{22}$ mid-chain branched alkyl alkoxylates, $BAE_R$, wherein x is 1-30, as discussed in U.S. Pat. Nos. 6,153,577; 6,020,303; and 6,093,856; f) alkylpolysaccharides as discussed in U.S. Pat. No. 4,565,647; specifically alkylpolyglycosides as discussed in U.S. Pat. Nos. 4,483,780 and 4,483,779; g) polyhydroxy fatty acid amides as discussed in U.S. Pat. No. 5,332,528; WO 92/06162; WO 93/19146; WO 93/19038; and WO 94/09099; and h) ether capped poly (oxyalkylated) alcohol surfactants as discussed in U.S. Pat. No. 6,482,994 and WO 01/42408.

In the laundry detergent compositions and other cleaning compositions herein, the detersive surfactant component may comprise combinations of anionic and nonionic surfactant materials. When this is the case, the weight ratio of anionic to nonionic will typically range from 10:90 to 90:10, more typically from 30:70 to 70:30.

Cationic surfactants are well known in the art and non-limiting examples of these include quaternary ammonium surfactants, which can have up to 26 carbon atoms. Additional examples include a) alkoxylate quaternary ammonium (AQA) surfactants as discussed in U.S. Pat. No. 6,136,769; b) dimethyl hydroxyethyl quaternary ammonium as discussed in U.S. Pat. No. 6,004,922; c) polyamine cationic surfactants as discussed in WO 98/35002; WO 98/35003; WO 98/35004; WO 98/35005; and WO 98/35006; d) cationic ester surfactants as discussed in U.S. Pat. Nos. 4,228,042; 4,239,660; 4,260,529; and 6,022,844; and e) amino surfactants as discussed in U.S. Pat. No. 6,221,825 and WO 00/47708, specifically amido propyldimethyl amine (APA).

Non-limiting examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaine, including alkyl dimethyl betaine and cocodimethyl amidopropyl betaine, $C_8$-$C_{18}$ (preferably $C_{12}$-$C_{18}$) amine oxides and sulfo and hydroxy betaines, such as N-alkyl-N,N-dimethylammino-1-propane sulfonate where the alkyl group can be $C_8$-$C_{18}$, preferably $C_{10}$-$C_{14}$.

Non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 at column 19, lines 18-35, for examples of ampholytic surfactants.

In another aspect of the present disclosure, the fabric care compositions disclosed herein, may take the form of granular laundry detergent compositions. Such compositions comprise the dispersant polymer of the present disclosure to provide soil and stain removal and anti-redeposition, suds boosting, and/or soil release benefits to fabric washed in a solution containing the detergent. Typically, the granular laundry detergent compositions are used in washing solutions at a level of from about 0.0001% to about 0.05%, or even from about 0.001% to about 0.01% by weight of the washing solution.

Granular detergent compositions of the present disclosure may include any number of conventional detergent ingredients. For example, the surfactant system of the detergent composition may include anionic, nonionic, zwitterionic, ampholytic and cationic classes and compatible mixtures thereof. Detergent surfactants for granular compositions are described in U.S. Pat. Nos. 3,664,961 and 3,919,678. Cationic surfactants include those described in U.S. Pat. Nos. 4,222,905 and 4,239,659.

Non-limiting examples of surfactant systems include the conventional $C_{11}$-$C_{18}$ alkyl benzene sulfonates ("LAS") and primary, branched-chain and random $C_{10}$-$C_{20}$ alkyl sulfates ("AS"), the $C_{10}$-$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$-$C_{18}$ alkyl alkoxy sulfates ("$AE_xS$"; especially EO 1-7 ethoxy sulfates), $C_{10}$-$C_{18}$ alkyl alkoxy carboxylates (especially the EO 1-5 ethoxycarboxylates), the $C_{10}$-$C_{18}$ glycerol ethers, the $C_{10}$-$C_{18}$ alkyl polyglycosides and their corresponding sulfated polyglycosides, and $C_{12}$-$C_{18}$ alpha-sulfonated fatty acid esters. If desired, the conventional nonionic and amphoteric surfactants such as the $C_{12}$-$C_{18}$ alkyl ethoxylates ("AE") including the so-called narrow peaked alkyl ethoxylates and $C_6$-$C_{12}$ alkyl phenol alkoxylates (especially ethoxylates and mixed ethoxy/propoxy), $C_{12}$-$C_{18}$ betaines and sulfobetaines ("sultaines"), $C_{10}$-$C_{18}$ amine oxides, and the like, can also be included in the surfactant system. The $C_{10}$-$C_{18}$ N-alkyl polyhydroxy fatty acid amides can also be used. See WO 92/06154. Other sugar-derived surfactants include the N-alkoxy polyhydroxy fatty acid amides, such as $C_{10}$-$C_{18}$N-(3-methoxypropyl) glucamide. The N-propyl through N-hexyl $C_{12}$-$C_{18}$ glucamides can be used for low sudsing. $C_{10}$-$C_{20}$ conventional soaps may also be used. If high sudsing is desired, the branched-chain $C_{10}$-$C_{16}$ soaps may be used. Mixtures of anionic and nonionic surfactants are especially useful. Other conventional useful surfactants are listed in standard texts.

The cleaning composition can, and in certain embodiments preferably does, include a detergent builder. Builders are generally selected from the various water-soluble, alkali metal, ammonium or substituted ammonium phosphates, polyphosphates, phosphonates, polyphosphonates, carbonates, silicates, borates, polyhydroxy sulfonates, polyacetates, carboxylates, and polycarboxylates. Preferred are the alkali metals, especially sodium, salts of the above. Preferred for use herein are the phosphates, carbonates, silicates, $C_{10}$-$C_{18}$ fatty acids, polycarboxylates, and mixtures thereof. More preferred are sodium tripolyphosphate, tetrasodium pyrophosphate, citrate, tartrate mono- and di-succinates, sodium silicate, and mixtures thereof.

Specific examples of inorganic phosphate builders are sodium and potassium tripolyphosphate, pyrophosphate, polymeric metaphosphate having a degree of polymerization of from about 6 to 21, and orthophosphates. Examples of polyphosphonate builders are the sodium and potassium salts of ethylene diphosphonic acid, the sodium and potassium salts of ethane 1-hydroxy-1,1-diphosphonic acid and the sodium and potassium salts of ethane-1,1,2-triphosphonic acid. Other phosphorus builder compounds are disclosed in U.S. Pat. Nos. 3,159,581; 3,213,030; 3,422,021; 3,422,137; 3,400,176; and 3,400,148. Examples of non-phosphorus, inorganic builders are sodium and potassium carbonate, bicarbonate, sesquicarbonate, tetraborate decahydrate, and silicates having a weight ratio of $SiO_2$ to alkali metal oxide of from about 0.5 to about 4.0, preferably from about 1.0 to about 2.4. Water-soluble, non-phosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid.

Polymeric polycarboxylate builders are set forth in U.S. Pat. No. 3,308,067. Such materials include the water-soluble salts of homo- and copolymers of aliphatic carboxylic acids such as maleic acid, itaconic acid, mesaconic acid, fumaric acid, aconitic acid, citraconic acid and methylenemalonic acid. Some of these materials are useful as the water-soluble anionic polymer as hereinafter described, but only if in intimate admixture with the non-soap anionic surfactant. Other suitable polycarboxylates for use herein are the polyacetal carboxylates described in U.S. Pat. Nos. 4,144,226 and 4,246,495.

Water-soluble silicate solids represented by the formula $SiO_2.M_2O$, M being an alkali metal, and having a $SiO_2$:$M_2O$ weight ratio of from about 0.5 to about 4.0, are useful salts in the detergent granules of this disclosure at levels of from about 2% to about 15% on an anhydrous weight basis. Anhydrous or hydrated particulate silicate can be utilized, as well.

Any number of additional ingredients can also be included as components in the various detergent and cleaning compositions described herein. These include other detergency builders, bleaches, bleach activators, suds boosters or suds suppressors, anti-tarnish and anti-corrosion agents, soil suspending agents, soil release agents, germicides, pH adjusting agents, non-builder alkalinity sources, chelating agents, smectite clays, enzymes, enzyme-stabilizing agents and perfumes. See U.S. Pat. No. 3,936,537.

Bleaching agents and activators are described in U.S. Pat. Nos. 4,412,934 and 4,483,781. Chelating agents are also described in U.S. Pat. No. 4,663,071 from column 17, line 54 through column 18, line 68. Suds modifiers are also optional ingredients and are described in U.S. Pat. Nos. 3,933,672 and 4,136,045. Suitable smectite clays for use herein are described in U.S. Pat. No. 4,762,645 column 6, line 3 through column 7, line 24. Suitable additional detergency builders for use herein are enumerated in U.S. Pat. No. 3,936,537 at column 13, line 54 through column 16, line 16, and in U.S. Pat. No. 4,663,071.

In yet another aspect of the present disclosure, the fabric care compositions disclosed herein, may take the form of rinse added fabric conditioning compositions. Such compositions may comprise a fabric softening active and the dispersant polymer of the present disclosure, to provide a stain repellency benefit to fabrics treated by the composition, typically from about 0.00001 wt. % (0.1 ppm) to about 1 wt. % (10,000 ppm), or even from about 0.0003 wt. % (3 ppm) to about 0.03 wt. % (300 ppm) based on total rinse added fabric conditioning composition weight. In another specific embodiment, the compositions are rinse added fabric conditioning compositions. Examples of typical rinse added conditioning composition can be found in U.S. Provisional Patent Application Ser. No. 60/687,582 filed on Oct. 8, 2004.

Adjunct Materials

While not essential for the purposes of the present disclosure, the non-limiting list of adjuncts illustrated hereinafter are suitable for use in various embodiments of the cleaning compositions and may be desirably incorporated in certain embodiments of the disclosure, for example to assist or enhance performance, for treatment of the substrate to be cleaned, or to modify the aesthetics of the composition as is the case with perfumes, colorants, dyes or the like. It is understood that such adjuncts are in addition to the components that were previously listed for any particular embodiment. The total amount of such adjuncts may range from about 0.1% to about 50%, or even from about 1% to about 30%, by weight of the cleaning composition.

The precise nature of these additional components, and levels of incorporation thereof, will depend on the physical form of the composition and the nature of the operation for which it is to be used. Suitable adjunct materials include, but are not limited to, polymers, for example cationic polymers, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282; 6,306,812; and 6,326,348.

As stated, the adjunct ingredients are not essential to the cleaning compositions. Thus, certain embodiments of the compositions do not contain one or more of the following adjuncts materials: bleach activators, surfactants, builders, chelating agents, dye transfer inhibiting agents, dispersants, enzymes, and enzyme stabilizers, catalytic metal complexes, polymeric dispersing agents, clay and soil removal/anti-redeposition agents, brighteners, suds suppressors, dyes, additional perfumes and perfume delivery systems, structure elasticizing agents, fabric softeners, carriers, hydrotropes, processing aids and/or pigments. However, when one or more adjuncts are present, such one or more adjuncts may be present as detailed below:

Surfactants—The compositions according to the present disclosure can comprise a surfactant or surfactant system wherein the surfactant can be selected from nonionic and/or anionic and/or cationic surfactants and/or ampholytic and/or zwitterionic and/or semi-polar nonionic surfactants. The surfactant is typically present at a level of from about 0.1%, from about 1%, or even from about 5% by weight of the cleaning compositions to about 99.9%, to about 80%, to about 35%, or even to about 30% by weight of the cleaning compositions.

Builders—The compositions of the present disclosure can comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3,5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The compositions herein may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The compositions of the present disclosure may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The compositions of the present disclosure can also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The compositions can comprise one or more detergent enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in compositions, for example, detergents can be stabilized by various techniques. The enzymes employed herein can be stabilized by the presence of water-soluble sources of calcium and/or magnesium ions in the finished compositions that provide such ions to the enzymes.

Catalytic Metal Complexes—The compositions may include catalytic metal complexes. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243.

If desired, the compositions herein can be catalyzed by means of a manganese compound. Such compounds and levels of use are well known in the art and include, for example, the manganese-based catalysts disclosed in U.S. Pat. No. 5,576,282.

Cobalt bleach catalysts useful herein are known, and are described, for example, in U.S. Pat. Nos. 5,597,936 and 5,595,967. Such cobalt catalysts are readily prepared by known procedures, such as taught for example in U.S. Pat. Nos. 5,597,936, and 5,595,967.

Compositions herein may also suitably include a transition metal complex of a macropolycyclic rigid ligand ("MRL").

As a practical matter, and not by way of limitation, the compositions and cleaning processes herein can be adjusted to provide on the order of at least one part per hundred million of the benefit agent MRL species in the aqueous washing medium, and may provide from about 0.005 ppm to about 25 ppm, from about 0.05 ppm to about 10 ppm, or even from about 0.1 ppm to about 5 ppm, of the MRL in the wash liquor.

Preferred transition-metals in the instant transition-metal bleach catalyst include manganese, iron and chromium. Preferred MRLs herein are a special type of ultra-rigid ligand that is cross-bridged such as 5,12-diethyl-1,5,8,12-tetraazabicyclo[6.6.2]hexadecane. Suitable transition metal MRLs are readily prepared by known procedures, such as taught, for example, in WO 00/32601, and U.S. Pat. No. 6,225,464.

Processes of Making Cleaning Compositions

The cleaning compositions, such as, but not limited to, the fabric care compositions of the present disclosure can be formulated into any suitable form and prepared by any process chosen by the formulator, non-limiting examples of which are described in U.S. Pat. Nos. 5,879,584; 5,691,297; 5,574,005; 5,569,645; 5,565,422; 5,516,448; 5,489,392; and 5,486,303.

In one aspect, the cleaning compositions disclosed herein may be prepared by combining the components thereof in any convenient order and by mixing, e.g., agitating, the resulting component combination to form a phase stable cleaning composition. In one aspect, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

In another aspect of producing liquid cleaning compositions, the modified lignin polymer may first be combined with one or more liquid components to form a modified lignin polymer premix, and this modified lignin polymer premix is added to a composition formulation containing a substantial portion, for example more than 50% by weight, more than 70% by weight, or even more than 90% by weight, of the balance of components of the cleaning composition. For example, in the methodology described above, both the modified lignin polymer premix and the enzyme component are added at a final stage of component additions. In another aspect, the modified lignin polymer is encapsulated prior to addition to the detergent composition, the encapsulated modified lignin polymer is suspended in a structured liquid, and the suspension is added to a composition formulation containing a substantial portion of the balance of components of the cleaning composition.

Various techniques for forming cleaning compositions in such solid forms are well known in the art and may be used herein. In one aspect, when the cleaning composition, such as a fabric care composition, is in the form of a granular particle, the modified lignin polymer is provided in particulate form, optionally including additional but not all components of the cleaning composition. The modified lignin polymer particulate is combined with one or more additional particulates containing a balance of components of the cleaning composition. Further, the modified lignin polymer, optionally including additional but not all components of the cleaning composition may be provided in an encapsulated form, and the modified lignin polymer encapsulate is combined with particulates containing a substantial balance of components of the cleaning composition.

Methods of Using Fabric Care Compositions

The fabric care compositions disclosed in the present specification may be used to clean or treat a fabric, such as those described herein. Typically at least a portion of the fabric is contacted with an embodiment of the aforementioned fabric care compositions, in neat form or diluted in a liquor, for example, a wash liquor and then the fabric may be optionally washed and/or rinsed. In one aspect, a fabric is optionally washed and/or rinsed, contacted with an embodiment of the aforementioned fabric care compositions and then optionally washed and/or rinsed. For purposes of the present disclosure, washing includes but is not limited to, scrubbing, and mechanical agitation. The fabric may comprise most any fabric capable of being laundered or treated.

The fabric care compositions disclosed in the present specification can be used to form aqueous washing solutions for use in the laundering of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the fabric care composition, such as the liquid detergent compositions disclosed in the present specification, may be added to water to form aqueous laundering solutions that may comprise from about 500 to about 7,000 ppm or even from about 1,000 to about 3,000 pm of fabric care composition.

In one aspect, the fabric care compositions may be employed as a laundry additive, a pre-treatment composition and/or a post-treatment composition.

While various specific embodiments have been described in detail herein, the present disclosure is intended to cover various different combinations of the disclosed embodiments and is not limited to those specific embodiments described herein. The various embodiments of the present disclosure may be better understood when read in conjunction with the following representative examples. The following representative examples are included for purposes of illustration and not limitation.

Test Methods

Average Molecular Weight

Molecular weight of lignin and their derivatives, such as the modified lignin polymers of the present disclosure is determined by Size Exclusion Chromatography with a Multi-Angle Light Scattering detector (SEC/MALLS). The analysis is performed using two Waters linear μstyrogel HT columns using DMSO with 0.1 wt % LiBr at 0.8 mL/min and Wyatt Technology DAWN EOS/rEX detection instruments. Data analysis is performed by Wyatt Astra software. A literature value of 0.117 is used for the dn/dc for lignin sulfonate in DMSO. W. Q. Qean and D. A. I. Goring, *J. Appl. Polym. Sci.,* 14, 1115 (1970). The percent active is determined using thermogravimetric analysis (TGA).

EXAMPLES

Example 1

Synthesis of Quaternized Lignin Sulfonate

In this Example, lignin sulfonate is modified to produce an amphoteric modified lignin polymer having anionic and quaternary ammonium nitrogen containing substitution.

TABLE 1

Results from Quaternization of Lignin Sulfonate

| Lignin Source | Reaction Type | Conditions | Yield g (%) | Wt % N substituent |
|---|---|---|---|---|
| Lignotech DP 524 | Quat | 5 h 55° C., MeOH | 7.39 g, (25%) | 0.97 |
| Lignotech DP 524 | Quat | 5 h 55° C., EtOH | | 0.45 (calc) |
| Lignotech DP 524 | Quat | 5 h 55° C., EtOH | 8.08 g (40%) | 0.18 (calc) |
| Lignotech DP 524 | Quat | 5 h 55° C., EtOH | 8.01 g (40%) | 0.05 (calc) |
| Tembec ARBO A02 | Quat | 5 h 55° C., EtOH | 29.51 g (76%) | 2.41 |
| Tembec ARBO A02 | Quat | 5 h 55° C., EtOH | 27.48 g (69%) | 1.77 |
| Tembec ARBO A02 | Quat | 5 h 55° C., EtOH | 28.64 g (72%) | 1.88 |

Lignin sulfonates from two sources (Borregaard/Lignotech and Tembec Inc.) are modified to install quaternary ammonium substituents. QUAB® 151 (available from QUAB Chemicals, Saddle Brook, N.J.) is reacted with lignin sulfonate (10 wt % in water) at a pH of 11.5 for 5 hours at 55° C. The base catalyst is neutralized with hydrochloric acid and the crude reaction mixture is poured into ethanol to precipitate the modified lignin. The modified lignin polymer is collected by filtration and dried under vacuum at 50° C. for 16 hours. Yield is typically 40% for Borregaard/Lignotech DP524 lignin and 75 wt % for Tembec ARBO A02 lignin. Results for the quaternization of these lignins are presented in Table 1.

Example 2

Synthesis of Alkoxy Lignin Sulfonate

In this Example, lignin sulfonate is modified to produce a modified lignin polymer having anionic and alkoxy containing substitution.

2-Hydroxybutyl lignin is prepared by reacting 1,2-epoxybutane and Tembec ARBO A02 lignin sulfonate (10 wt % in water, available from Tembec Ind., Quebec, Canada) at a pH of 11.5 for 6 hours at 55° C. The base catalyst is neutralized with hydrochloric acid and the crude reaction mixture is poured into ethanol to precipitate the modified lignin. The 2-hydroxybutyl lignin is collected by filtration and dried under vacuum at 50° C. for 16 hours. Yield is 72 wt %. The resulting modified lignin polymer has an alkoxy substitution weight percentage of 3.7%, by NMR. Results for alkoxylation are presented in Table 2.

TABLE 2

Results from Alkoxylation of Lignin Sulfonate

| Lignin Source | Reaction Type | Conditions | Yield g (%) | Comment |
|---|---|---|---|---|
| Tembec ARBO A02 | Butoxylation | 6 h 55° C., EtOH | 28.64 g (72%) | 3.7 Wt % Hydroxybutyl found by NMR |

Example 3

Synthesis of Polypropylene Glycol Modified Lignin Sulfonate

In this Example, lignin sulfonate is modified to produce a modified lignin polymer having anionic and polypropylene glycol containing substitution.

Lignin sulfonate (Tembec ARBO A02) is derivatized with the glycidyl ether of poly(propylene glycol) monobutyl ether to prepare polypropylene oxide monobutyl ether and sulfonate modified lignin. The derivatizing agent is prepared by reacting epichlorohydrin with poly(propylene glycol) monobutyl ether (Mn=469 by NMR, available from Sigma-Aldrich, Milwaukee, Wis., catalog no. 438103).

Sodium hydride is washed 3 times with hexane, dried with a stream of nitrogen and added to anhydrous DMSO with agitation. The reagents are allowed to react overnight under a head pressure of nitrogen and form an almost clear reagent. Tembec ARBO 02 (available from Tembec Ind., Quebec, Canada) is dried and added to the dimsyl reagent and reacted overnight. Glycidyl polypropylene oxide monobutyl ether is added and allowed to react 65 hours. The mixture is neutralized with 1N HCl and dialyzed against water for 16 hours. The product is freeze dried, then dried in a vacuum oven for 16 hours. The yield of modified lignin polymer is 16.2 grams (54%). Proton NMR spectroscopy is performed and indicates 15 wt % polypropylene oxide (PPO) substitution. Results for polypropoxylation of the lignin sulfonate are presented in Table 3.

TABLE 3

Results from Polypropoxylation of Lignin Sulfonate

| Lignin Source | Reaction Type | Conditions | Yield g (%) | Comment |
|---|---|---|---|---|
| Tembec ARBO A02 | PPO | 65 h RT; Dialysis | 16.2 g (54%) | 15 wt % PPO by NMR, EtOH soluble |

Example 4

Powder Laundry Detergent Formulation

In this Example, four sample formulations for a powder laundry detergent are prepared using the modified lignin polymer according to embodiments of the present disclosure. The modified lignin polymer is added to the formulations in an amount ranging from 1.0% to 3.0% by weight. The powder detergent formulations are presented in Table 4.

TABLE 4

Powder Laundry Detergent Formulations

| Ingredients | A Wt. % | B Wt. % | C Wt. % | D Wt. % |
|---|---|---|---|---|
| Sodium alkylbenzenesulfonate | 16.0000 | 14.0000 | 12.0000 | 7.9 |
| Sodium alkyl alcohol ethoxylate (3) sulfate | — | — | — | 4.73 |
| Sodium mid-cut alkyl sulfate | — | 1.5000 | 1.5000 | — |
| Alkyl dimethyl hydroxyethyl quaternary amine (chloride) | — | — | — | 0.5 |
| Alkyl ethoxylate | 1.3000 | 1.3000 | 1.3000 | — |
| Polyamine[1] | — | — | — | 0.79 |
| Nonionic Polymer[2] | 1.0000 | 1.0000 | 1.0000 | 1.0 |
| Carboxymethylcellulose | 0.2000 | 0.2000 | 0.2000 | 1.0 |
| Sodium polyacrylate | — | — | — | — |
| Sodium polyacrylate/maleate polymer | 0.7000 | 0.7000 | 0.7000 | 3.5 |
| Modified Lignin[5] | 1.0000 | 1.0000 | 1.0000 | 3.0000 |
| Sodium tripolyphosphate | 10.0000 | 5.0000 | — | — |
| Zeolite | 16.0000 | 16.0000 | 16.0000 | — |
| Citric Acid | — | — | — | 5.0 |
| Sodium Carbonate | 12.5000 | 12.5000 | 12.5000 | 25.0 |
| Sodium Silicate | 4.0 | 4.0 | 4.0 | — |
| Enzymes[3] | 0.30 | 0.30 | 0.30 | 0.5 |
| Minors including moisture[4] | balance | balance | balance | balance |

[1]Hexamethylenediamine ethoxylated to 24 units for each hydrogen atom bonded to a nitrogen, quaternized.
[2]Comb polymer of polyethylene glycol and polyvinylacetate
[3]Enzyme cocktail selected from known detergent enzymes including amylase, cellulase, protease, and lipase.
[4]Balance to 100% can, for example, include minors like optical brightener, perfume, suds suppresser, soil dispersant, soil release polymer, chelating agents, bleach additives and boosters, dye transfer inhibiting agents, aesthetic enhancers (example: Speckles), additional water, and fillers, including sulfate, $CaCO_3$, talc, silicates, etc.
[5]Lignin sulfonate quaternized to 0.97 wt % nitrogen

Example 5

Heavy Duty Liquid Laundry Detergent Formulation

In this Example, three sample formulations for a heavy duty liquid (HDL) laundry detergent are prepared using the modified lignin polymer according to embodiments of the present disclosure. The modified lignin polymer is added to the formulations in an amount ranging from 0.5% to 2.0% by weight. The HDL laundry detergent formulations are presented in Table 5.

TABLE 5

Heavy Duty Liquid Laundry Detergent Formulations

| Ingredient | A Wt % | B Wt % | C Wt % |
|---|---|---|---|
| Sodium alkyl ether sulfate | 20.5 | 20.5 | 20.5 |
| Branched alcohol sulfate | 5.8 | 5.8 | 5.8 |
| Linear alkylbenzene sulfonic acid | 2.5 | 2.5 | 2.5 |
| Alkyl ethoxylate | 0.8 | 0.8 | 0.8 |
| Amine oxide | 0 | 0.5 | 2 |
| Citric acid | 3.5 | 3.5 | 3.5 |
| Fatty acid | 2.0 | 2.0 | 2.0 |
| Protease | 0.7 | 0.7 | 0.7 |
| Amylase | 0.37 | 0.37 | 0.37 |
| Borax | 3.0 | 3.0 | 3.0 |
| Calcium and sodium formate | 0.22 | 0.22 | 0.22 |
| Amine ethoxylate polymers | 1.2 | 0.5 | 1.0 |
| Zwitterionic amine ethoxylate polymer | 1.0 | 2.0 | 1.0 |
| Modified Lignin[1] | 0.5 | 1.0 | 2.0 |
| DTPA[2] | 0.25 | 0.25 | 0.25 |
| Fluorescent whitening agent | 0.2 | 0.2 | 0.2 |
| Ethanol | 2.9 | 2.9 | 2.9 |
| Propanediol | 5.0 | 5.0 | 5.0 |
| Diethylene glycol | 2.56 | 2.56 | 2.56 |
| Polyethylene glycol 4000 | 0.11 | 0.11 | 0.11 |
| Ethanolamine | 2.7 | 2.7 | 2.7 |
| Sodium hydroxide | 3.67 | 3.67 | 3.67 |
| Sodium cumene sulfonate | 0 | 0.5 | 1 |
| Silicone suds suppressor | 0.01 | 0.01 | 0.01 |
| Perfume | 0.5 | 0.5 | 0.5 |
| Acid Blue 7[3] | 0.01 | 0.01 | 0.01 |
| Opacifier[4] | 0.01 | 0.01 | 0.01 |
| Water | balance | balance | balance |
| | 100.0% | 100.0% | 100.0% |

[1]Lignin sulfonate quatenized to 0.97 wt. % nitrogen
[2]Diethylenetriaminepentaacetic acid, sodium salt
[3]A non-tinting dye used to adjust formula color
[4]Acusol OP 301

Example 6

Automatic Dishwasher Detergent Formulation

In this Example, five sample formulations for an automatic dishwasher detergent are prepared using the modified lignin polymer according to embodiments of the present disclosure.

The modified lignin polymer is added to the formulations in an amount ranging from 0.05% to 15% by weight. The automatic dishwasher detergent formulations are presented in Table 6.

TABLE 6

Automatic Dishwasher Detergent Formulations

| Ingredients | A Wt. % | B Wt. % | C Wt. % | D Wt. % | E Wt. % |
|---|---|---|---|---|---|
| Polymer dispersant[1] | 0.5 | 5 | 6 | 5 | 5 |
| Carbonate | 35 | 40 | 40 | 35-40 | 35-40 |
| Sodium tripolyphosphate | 0 | 6 | 10 | 0-10 | 0-10 |
| Silicate soilds | 6 | 6 | 6 | 6 | 6 |
| Bleach and Bleach activators | 4 | 4 | 4 | 4 | 4 |
| Enzymes | 0.3-0.6 | 0.3-0.6 | 0.3-0.6 | 0.3-0.6 | 0.3-0.6 |
| Disodium citrate dihydrate | 0 | 0 | 0 | 2-20 | 0 |
| Nonionic surfactant[2] | 0 | 0 | 0 | 0 | 0.8-5 |
| Modified lignin polymer | 0.05-15 | 0.05-15 | 0.05-15 | 0.05-15 | 0.05-15 |
| Water, sulfate, perfume, dyes and other adjucts | Balance to 100% | Balance to 100% | Balance to 100% | Balance to 100% | Balance to 100% |

[1]Anionic polymers such as Acusol, Alcosperse and other modified polyacrylic acid polymers.
[2]Such as SLF-18 polytergent from Olin Corporation

Example 7

Shampoo Formulation

In this Example, six sample formulations for a shampoo are prepared using the modified lignin polymer according to embodiments of the present disclosure. The modified lignin polymer is added to the shampoo formulations in an amount ranging from 0.05% to 15% by weight. The shampoo formulations are presented in Table 7.

TABLE 7

Shampoo Formulations

| Ingredients | A Wt. % | B Wt. % | C Wt. % | D Wt. % | E Wt. % | F Wt. % |
|---|---|---|---|---|---|---|
| Polyquaterium 10[1] | 0.5 | — | — | 0.5 | — | — |
| Polyquaterium 10[2] | — | 0.25 | — | — | — | — |
| Guar hydroxypropyl trimonium chloride[3] | — | — | — | — | 0.1 | 0.2 |
| Polyquaterium 10[4] | — | — | 0.1 | — | — | — |
| Sodium laureth sulfate (SLE3S-29% active)[5] | 41.38 | 51.72 | 41.38 | 41.38 | 24.12 | 27.58 |
| Sodium lauryl sulfate (SLS-29% active)[6] | 10.34 | 17.24 | 6.9 | 6.9 | 24.12 | 22.07 |
| Dimethiconol microemulsion A[7] | 4.0 | — | 1.0 | — | 4.0 | — |
| Low D4 dimethiconol microemulsion B[8] | — | — | — | 8.0 | — | 8.0 |
| Dimethiconol microemulsion C[9] | — | 1.0 | — | — | — | — |
| Disodium coco amphodiacetate[10] | 5.0 | — | 5.0 | — | — | — |
| Cocoamdopropyl betaine[11] | — | — | 2.0 | 6.67 | 6.67 | 6.67 |
| PPG-2 hydroxyethyl coco-isostearamide[12] | 2.0 | 2.0 | 2.0 | 2.0 | 2.0 | 2.0 |
| Magnesium chloride hexahydrate[13] | 0.5 | — | — | 0.5 | — | — |
| Sodium chloride[14] | 0.5 | 0.75 | 1.0 | 0.5 | 1.0 | 1.0 |
| Fragrance | 0.55 | 0.55 | 0.55 | 0.5 | 0.5 | 0.5 |
| Preservatives, pH adjusters | up to 1% | up to 1% | up to 1% | up to 1% | up to 1% | up to 1% |
| Modified lignin polymer | 0.05-15 | 0.05-15 | 0.05-15 | 0.05-15 | 0.05-15 | 0.05-15 |
| Water | Balance to 100% | Balance to 100% | Balance to 100% | Balance to 100% | Balance to 100% | Balance to 100% |

[1]UCare Polymer JR30M, MW = 2.0 MM, charge density = 1.32 meq/g, Dow Chemical.
[2]UCare PolymerKG30M, MW = 2.0 MM, Charge density = 1.96 meq/g, Dow Chemical.
[3]Jaguar Excel, Rhodia.
[4]UCarePolymer JP, MW = 2.0 MM, charge density = 0.7 meq/g, Dow Chemical.
[5]Sodlium laureth sulfate at 29% active with average of approx. 3 moles ethoxylation, P&G.
[6]Sodium lauryl sulfate at 29% active, P&G.
[7]Dow Corning 2-1865, internal phase viscosity = 44,000 cps, 30 nm particle size dimethiconol using TEA dodecyl benzene sulfonate & laureth 23 as primary surfactants, 25% active silicone.
[8]Dow Corning 2-1865, internal phase viscosity = 34,000 cps, 30 nm particle size dimethiconol using TEA dodecyl benzene sulfonate & laureth 23 as primary surfactants, 25% active.
[9]Dow Corning 2-1865, internal phase viscosity = 25,400 cps, 30 nm particle size dimethiconol using TEA dodecyl benzene sulfonate & laureth 23 as primary surfactants, 25% active silicone.
[10]Miranol C2M conc NP, 40% active, Rhodia.
[11]Tegobetaine F-B, 30% active, Goldschmidt Chemicals.
[12]Promidium 2, Unichema.
[13]Magnesium chloride hexahydrate, Fisher Chemicals.
[14]Sodium chloride USP (food grade), Morton.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Disclosure are, in relevant part, incorporated herein by reference; the citation of any document is not to be construed as an admission that it is prior art with respect to the present disclosure. To the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A modified lignin polymer comprising:
   a randomly substituted lignin backbone comprising substituted lignin monomer residues and unsubstituted lignin monomer residues, wherein at least two or more of the hydroxyl groups on the randomly substituted lignin backbone have been substituted with R substituent groups,
   wherein each R substituent group is independently an R substituent type selected from the group consisting of quaternary nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types;

wherein the modified lignin polymer has a weight average molecular weight ranging from 2,000 Daltons to 300,000 Daltons.

2. The modified lignin polymer of claim 1, wherein the modified lignin polymer comprises substituted lignin monomer residues and unsubstituted lignin monomer residues selected from the group consisting of substituted and unsubstituted residues of p-coumaryl alcohol, coniferyl alcohol, sinapyl alcohol, derivatives thereof, and mixtures thereof.

3. The modified lignin polymer of claim 1, wherein the modified lignin polymer is incorporated into a cleaning composition, a fabric care composition, a dish cleaning composition, a home care composition, or a personal care composition.

4. The modified lignin polymer of claim 1, wherein the each R substituent is attached to the lignin backbone at an oxygen on the lignin backbone.

5. The modified lignin polymer of claim 1, wherein each quaternary nitrogen containing substituent $R^1$ independently has a structure according to Formula II:

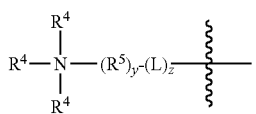

where each $R^4$ is selected from the group consisting of $CH_3$, and linear or branched, saturated or unsaturated $C_2$-$C_{18}$ alkyl, $R^5$ is a linear or branched, saturated or unsaturated $C_2$-$C_{18}$ alkyl chain or a linear or branched, saturated or unsaturated secondary hydroxy($C_2$-$C_{18}$)alkyl chain; L is a linking group selected from the group consisting of —O—, —C(O)O—, —NR$^6$—, —C(O)NR$^6$—, and —NR$^6$C(O)NR$^6$—, where $R^6$ is H or $C_1$-$C_6$ alkyl; y has a value of 0 or 1; and z has a value of 0 or 1.

6. The modified lignin polymer of claim 1, wherein each anionic substituent $R^2$ independently has a structure according to Formula III:

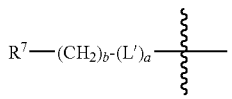

wherein $R^7$ is an anionic group selected from the group consisting of carboxylate, carboxymethyl, succinate, sulfate, sulfonate, arylsulfonate, phosphate, phosphonate, dicarboxylate, and polycarboxylate; L' is a linking group selected from the group consisting of —O—, —C(O)O—, —NR$^8$—, —C(O)NR$^8$—, and —NR$^8$C(O)NR$^8$—, where $R^8$ is H or $C_1$-$C_6$ alkyl; a has a value of 0 or 1; and b is an integer from 0 to 18.

7. The modified lignin polymer of claim 1, wherein each alkoxy substituent $R^3$ independently has a structure according to Formula IV:

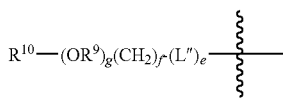

wherein e has a value of 0 or 1; f is an integer from 0 to 8; g is an integer from 0 to 50; L" is a linking group selected from the group consisting of —O—, —C(O)O—, —NR$^{11}$—, —C(O)NR$^{11}$—, and —NR$^{11}$C(O)NR$^{11}$—, where $R^{11}$ is H or $C_1$-$C_6$ alkyl; each $R^9$ is the group ethylene, propylene, butylene, or mixtures thereof; and $R^{10}$ is an end group selected from the group consisting of hydrogen, $C_1$-$C_{20}$ alkyl, hydroxy, —OR$^1$ and —OR$^2$.

8. The modified lignin polymer of claim 7, wherein $R^9$ has a structure —CH($R^{12}$)CH$_2$— where $R^{12}$ is hydrogen, methyl, or ethyl.

9. The modified lignin polymer of claim 1, further comprising one or more hydrophobic substituents $R^{13}$ attached to the lignin backbone at an oxygen, with a substitution weight percentage ranging from 0.1% to 50%, wherein each hydrophobic substituent $R^{13}$ independently has a structure selected from a linear or branched, saturated or unsaturated $C_1$-$C_{18}$ alkyl, a linear or branched, saturated or unsaturated $C_7$-$C_{18}$ alkylaryl, a linear or branched, saturated or unsaturated secondary hydroxy($C_2$-$C_{18}$)alkyl, or a hydrophobic polymer graft.

10. The modified lignin polymer of claim 1, wherein the randomly substituted lignin backbone is derived from a lignin selected from the group consisting of lignin sulfonates, Kraft lignins, soda lignins, organosolv lignins, softwood lignin, hardwood lignin, cellulosic grasses lignins, corn stover lignins, steam explosion lignins and combinations of any thereof.

11. A modified lignin polymer comprising:
a randomly substituted lignin backbone having a structure

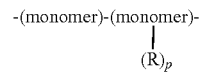

comprising substituted lignin monomer residues and unsubstituted lignin monomer residues selected from the group consisting of substituted and unsubstituted residues of p-coumaryl alcohol, coniferyl alcohol, sinapyl alcohol, derivatives thereof, and mixtures thereof, wherein at least two or more of the hydroxyl groups on the randomly substituted lignin backbone have been substituted with R substituent groups, where p is an integer from 1 to 3, and each R substituent group is independently R substituent types selected from the group consisting of:
quaternary nitrogen containing substituents $R^1$ with a substitution weight percentage ranging from 0% to 75%, each $R^1$ independently having a structure according to Formula II:

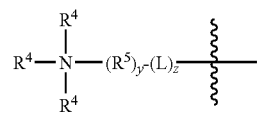

where each $R^4$ is selected from the group consisting of $CH_3$, and linear or branched, saturated or unsaturated $C_2$-$C_{18}$ alkyl, $R^5$ is a linear or branched, saturated or unsaturated $C_2$-$C_{18}$ alkyl chain or a linear or branched, saturated or unsaturated secondary hydroxy($C_2$-$C_{18}$)alkyl chain; L is a linking group selected from the group consisting of —O—, —C(O)O—, —NR$^6$—, —C(O)NR$^6$—, and —NR$^6$C(O)NR$^6$—, where $R^6$ is H or $C_1$-$C_6$ alkyl; y has a value of 0 or 1; and z has a value of 0 or 1;

anionic substituents $R^2$ with a substitution weight percentage ranging from 0% to 90%, each $R^2$ independently having a structure according to Formula III:

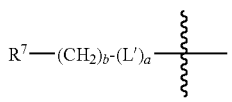

wherein $R^7$ is an anionic group selected from the group consisting of carboxylate, carboxymethyl, succinate, sulfate, sulfonate, arylsulfonate, phosphate, phosphonate, dicarboxylate, and polycarboxylate; L' is a linking group selected from the group consisting of —O—, —C(O)O—, —NR$^8$—, —C(O)NR$^8$—, and —NR$^8$C(O)NR$^8$—, where $R^8$ is H or $C_1$-$C_6$ alkyl; a has a value of 0 or 1; and b is an integer from 0 to 18;

alkoxy substituents $R^3$ with a substitution weight percentage ranging from 0% to 90%, each $R^3$ independently having a structure according to Formula IV:

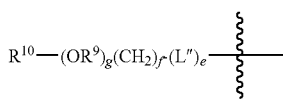

wherein e has a value of 0 or 1; f is an integer from 0 to 8; g is an integer from 0 to 50; L" is a linking group selected from the group consisting of —O—, —C(O)O—, —NR$^{11}$13, —C(O)NR$^{11}$—, and —NR$^{11}$C(O)NR$^{11}$—, where $R^{11}$ is H or $C_1$-$C_6$ alkyl; each $R^9$ is the group ethylene, propylene, butylene, or mixtures thereof; and $R^{10}$ is an end group selected from the group consisting of hydrogen, $C_1$-$C_{20}$ alkyl, hydroxy, —OR$^1$ and —OR$^2$; and combinations of any thereof,
provided that the randomly substituted lignin backbone comprises at least two different R substituent types and wherein the modified lignin polymer has a weight average molecular weight ranging from 2,000 Daltons to 300,000 Daltons.

12. A cleaning composition comprising a modified lignin polymer having a randomly substituted lignin backbone comprising:
substituted lignin monomer residues and unsubstituted lignin monomer residues, wherein at least two or more of the hydroxyl groups on the randomly substituted lignin backbone have been substituted with R substituent groups,
wherein each R substituent group is independently an R substituent type selected from the group consisting of nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types;
wherein the modified lignin polymer has a weight average molecular weight ranging from 2,000 Daltons to 300,000 Daltons.

13. The cleaning composition of claim 12, further comprising at least one or more adjuncts selected from the group consisting of bleach activators, surfactants, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, perfumes, perfume delivery systems, structure elasticizing agents, fabric softeners, carriers, hydrotropes, processing aids, and pigments.

14. The cleaning composition of claim 12, wherein the cleaning composition is a product selected from the group consisting of liquid laundry detergents, solid laundry detergents, laundry soap products, laundry spray treatment products, laundry pre-treatment products, hand dish washing detergents, automatic dishwashing detergents, a beauty care detergent, hard surface cleaning detergents, carpet cleaning detergents, a shampoo, and a household cleaning detergent.

15. A method for making a cleaning composition comprising:
adding a modified lignin polymer to the cleaning composition,
wherein the modified lignin polymer has a randomly substituted lignin backbone comprising:
substituted lignin monomer residues and unsubstituted lignin monomer residues, wherein at least two or more of the hydroxyl groups on the randomly substituted lignin backbone have been substituted with R substituent groups, wherein each R substituent group is independently an R substituent type selected from the group consisting of nitrogen containing substituents $R^1$ with a substitution weight percentage ranging from 0% to 75%, anionic substituents $R^2$ with a substitution weight percentage ranging from 0% to 90%, alkoxy substituents $R^3$ with a substitution weight percentage ranging from 0% to 90%, and combinations of any thereof, provided that the randomly substituted lignin backbone comprises at least two different R substituent types;
wherein the modified lignin polymer has a weight average molecular weight ranging from 2,000 Daltons to 300,000 Daltons.

16. The method of claim 15, further comprising:
adding at least one or more adjuncts selected from the group consisting of bleach activators, surfactants, builders, chelating agents, dye transfer inhibiting agents, dispersants, enzymes, enzyme stabilizers, catalytic metal complexes, polymeric dispersing agents, clay and soil removal/anti-redeposition agents, brighteners, suds suppressors, dyes, perfumes, perfume delivery systems, structure elasticizing agents, fabric softeners, carriers, hydrotropes, processing aids, and pigments to the cleaning composition.

17. The method of claim 15, further comprising:
modifying a lignin polymer by substituting at least two hydroxyl groups on a lignin polymer backbone with at least two R substituent groups.

18. A method of treating a fabric comprising:
contacting the fabric with an effective amount of a fabric care composition comprising the modified lignin polymer according to claim 11.

* * * * *